(12) United States Patent
Smets et al.

(10) Patent No.: US 9,890,351 B2
(45) Date of Patent: Feb. 13, 2018

(54) ENCAPSULATES

(75) Inventors: Johan Smets, Lubbeek (BE); Susana Fernandez Prieto, Benicarlo (ES); Steven Daryl Smith, Fairfield, OH (US); Todd Laurence Underiner, Cincinnati, OH (US); John August Wos, Mason, OH (US); Wolfgang Edgar Huhn, Blue Ash, OH (US); Heath A. Frederick, Harrison, OH (US); Marta Giamberini, Tarragona (ES); Bartosz Tylkowski, Tarragona (ES)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/569,254

(22) Filed: Aug. 8, 2012

(65) Prior Publication Data

US 2013/0039962 A1 Feb. 14, 2013

(51) Int. Cl.

| C11D 17/00 | (2006.01) |
|---|---|
| A61Q 13/00 | (2006.01) |
| A61K 8/11 | (2006.01) |
| C11D 3/37 | (2006.01) |
| C11D 3/48 | (2006.01) |
| C11D 3/50 | (2006.01) |
| A61Q 5/02 | (2006.01) |
| A61K 8/81 | (2006.01) |
| A61Q 19/10 | (2006.01) |
| A61Q 5/12 | (2006.01) |
| A61Q 15/00 | (2006.01) |
| A61Q 19/00 | (2006.01) |

(52) U.S. Cl.
CPC ............ *C11D 17/0039* (2013.01); *A61K 8/11* (2013.01); *A61K 8/8129* (2013.01); *A61K 8/8152* (2013.01); *A61Q 5/02* (2013.01); *A61Q 13/00* (2013.01); *A61Q 19/10* (2013.01); *C11D 3/373* (2013.01); *C11D 3/48* (2013.01); *C11D 3/505* (2013.01); *A61K 2800/412* (2013.01); *A61K 2800/47* (2013.01); *A61K 2800/81* (2013.01); *A61Q 5/12* (2013.01); *A61Q 15/00* (2013.01); *A61Q 19/00* (2013.01)

(58) Field of Classification Search
CPC .... A61K 2800/412; A61K 8/11; A61Q 13/00; A61Q 15/00; C11D 17/0039; C11D 3/505
See application file for complete search history.

(56) References Cited

U.S. PATENT DOCUMENTS

| 3,405,071 A * | 10/1968 | Reyes | 264/4.32 |
|---|---|---|---|
| 4,826,954 A * | 5/1989 | Suzuki | C08G 77/54 |
| | | | 528/15 |
| 4,900,556 A * | 2/1990 | Wheatley et al. | 424/450 |
| 5,366,881 A | 11/1994 | Singh et al. | |
| 6,013,122 A | 1/2000 | Klitzman et al. | |
| 6,383,500 B1 * | 5/2002 | Wooley | C08J 3/246 |
| | | | 424/401 |
| 6,491,903 B1 * | 12/2002 | Forster | C08J 3/246 |
| | | | 424/489 |
| 6,531,118 B1 * | 3/2003 | Gonzalez | A61K 8/49 |
| | | | 424/400 |
| 2010/0284924 A1 | 11/2010 | Zink et al. | |
| 2011/0180745 A1 * | 7/2011 | Margutti et al. | 252/62.51 R |
| 2011/0206751 A1 | 8/2011 | Li et al. | |
| 2011/0268778 A1 | 11/2011 | Dihora et al. | |
| 2012/0148647 A1 | 8/2012 | Walzel et al. | |
| 2012/0189681 A1 | 8/2012 | Macedo Taveres et al. | |
| 2012/0228520 A1 | 9/2012 | Tan et al. | |

FOREIGN PATENT DOCUMENTS

| JP | 2004-224828 | 8/2004 | |
|---|---|---|---|
| JP | 2011 046669 | 3/2011 | |
| WO | WO 0196010 A1 * | 12/2001 | ............. A01N 25/28 |

OTHER PUBLICATIONS

Richard A. Wolf, Paul V. Grosso, Alan E. Platt, Thomas L. Staples, Jerry E. White. Thermally Stable, Photoactive Polymerizable Diazenes. Applications in Polymer Technology. Journal of Polymer Science: Part A: Polymer Chemistry, vol. 37, 3203-3213 (1999).*
Higuchi et al. Photo-responsive behavior of a monolayer composed of an azobenzene containing polypeptide in the main chain. Colloid Polym Sci 273:1022-1027 (1995).*
Higuchi et al. Photo-responsive behavior of a monolayer composed of an azobenzene containing polypeptide in the main chain. Colloid Polym Sci 1995, 273:1022-1027.*
Tao et al. Self-Assembly, Optical Behavior, and Permeability of a Novel Capsule Based on an Azo Dye and Polyelectrolytes. Chem. Eur. J. 2004, 10:3397-3403.*
Wolf et al. Thermally stable, photoactive polymerizable diazenes. Applications in polymer technology. J. Polymer Science: Part A: Polymer Chemistry, 1999, 37:3203-3213.*
Rijcken, et al., "Triggered destabilization of polymeric micelles and vesicles by changing polymers polarity: An attractive tool for drug delivery", *Journal of Controlled Release*, Elsevier, vol. 102, No. 3, pp. 131-148, (Jul. 17, 2007).
International Search Report dated Dec. 6, 2012.
Guoqiang et al., "A Study on the Photocontrolled Release of Small Molecular Compound from Synthetic Copolymer Film Which Contain Azobenzene Groups", Institute of photographic chemistry, Academia Sinica, p. 230.

(Continued)

*Primary Examiner* — Robert A Wax
*Assistant Examiner* — Olga V Tcherkasskaya
(74) *Attorney, Agent, or Firm* — Jason J Camp; James F McBride

(57) ABSTRACT

The present application relates to encapsulates, compositions, products comprising such encapsulates, and processes for making and using such encapsulates. Such encapsulates comprise a core comprising a perfume and a shell that encapsulates said core, such encapsulates may optionally comprise a parametric balancing agent, such shell comprising one or more azobenzene moieties.

9 Claims, No Drawings

(56) References Cited

OTHER PUBLICATIONS

Tylkowski et al., "Preparation of a new lightly cross-linked liquid crystalline polyamide by interfacial polymerization. Application to the obtainment of microcapsules with photo-triggered release", European Polymer Journal 45, 2009, pp. 1420-1432.
Yang et al., "Formation of Polymer Vesicles by Liquid Crystal Amphiphilic Block Copolymers", Langmuir, 2006, vol. 22, No. 18, pp. 7907-7911.

\* cited by examiner

ENCAPSULATES

CROSS REFERENCE TO RELATED APPLICATION

This application claims priority to U.S. Provisional Application Ser. No. 61/522,086, filed Aug. 10, 2011.

FIELD OF THE INVENTION

The present application relates to encapsulates, compositions, products comprising such encapsulates, and processes for making and using such encapsulates.

BACKGROUND OF THE INVENTION

Benefit agents such as perfumes are expensive and may be less effective when employed at high levels in compositions such as personal care compositions, cleaning compositions and fabric care compositions. As a result, there is a desire to maximize the effectiveness of benefit agents. One manner of achieving that objective is to improve the delivery efficiency of the benefit agents. Unfortunately, it is difficult to improve the delivery efficiencies of benefit agents as they may be lost due to their physical or chemical characteristics, they may be incompatible with other compositional components or the situs that is treated, or they may be lost during post application processes such as rinsing or drying.

One method of improving the delivery efficiency of benefit agents is to encapsulate them so that the benefit agent is released via pressure that fractures the shell of the encapsulate. However, current encapsulated benefit agents can leak over time and current encapsulated benefit agents, in general, may not fracture and release the benefit agent when desired—particularly in consumer product applications where limited mechanical forces are available, inter alia drapery or upholstery refreshing, shampoos, conditioners and hair sprays or styling gels, and hard surface treatment applications, floor cleaners, dust removing products to name a few. In short, Applicants recognized that current encapsulates do not function as desired as such encapsulates only respond to ineffective and/or undesired external stimuli such as pressure. Applicants further recognized that the correct external stimuli for certain applications, are temperature, infrared radiation, visible light, and/or ultraviolet radiation. While not being bound by theory, Applicants believe that encapsulates having a shell that comprises one or more moieties that are sensitive to infrared radiation, visible light, and/or ultraviolet radiation, for example, azo-benzene moieties have a state of order and conformation that permits the encapsulate to respond to triggers such as the aforementioned species of electromagnetic radiation. Such response typically results in the release of all or a portion of the encapsulate's core material. Such encapsulate's response to the aforementioned species of electromagnetic radiation can be tailored by the judicious selection of the type and amount of the one or more shell moieties that are sensitive to infrared radiation, visible light, and/or ultraviolet radiation and the type and amount of the remaining moieties that make up the encapsulate's shell. In short, the encapsulates that are disclosed herein can be tailored such that, over the desired time frame, they have the desired leakage profile and release profile. In view of the current art encapsulates, such release characteristics are unexpected as the skilled artisan would expect that encapsulates that are triggered by the aforementioned species of electromagnetic radiation would, once exposed to a trigger, release all of their benefit agent.

SUMMARY OF THE INVENTION

The present application relates to encapsulates, compositions, products comprising such encapsulates, and processes for making and using such encapsulates. Such encapsulates comprise a core comprising a perfume and a shell that encapsulates said core, such encapsulates may optionally comprise a parametric balancing agent, such shell comprising one or more azobenzene moieties.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; products and/or methods relating to oral care including toothpastes, tooth gels, tooth rinses, denture adhesives, tooth whitening; over-the-counter health care including pain relievers, pet health and nutrition, and water purification.

As used herein, the term "cleaning and/or treatment composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the articles "a" and "an" when used in a claim, are understood to mean one or more of what is claimed or described.

As used herein, the terms "include", "includes" and "including" are meant to be synonymous with the phrase "including but not limited to".

As used herein, the term "solid" means granular, powder, bar and tablet product forms.

As used herein, the term "situs" includes paper products, fabrics, garments, hard surfaces, hair and skin.

As used herein, a "parametric balancing agent" is a material that can be employed to alter one or more of the following properties of an encapsulate and/or the encapsulate's core material: density, vapor pressure and/or cLogP. When a parametric balancing agent is used to alter the vapor pressure of an encapsulate and/or the encapsulate's core material, the boiling of such encapsulate and/or the encapsulate's core material is inherently altered.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Encapsulates and Compositions Comprising Encapsulates

The time period for determining the leakage profile of an encapsulate may include the time the encapsulate is in product and the time such product is in use. The satisfactory delivery of the content(s) of an encapsulate requires optimum capsule mechanical properties as if the capsule is too strong, it never releases its content and if a capsule is too weak, it breaks too soon thus releasing its content prematurely. In addition, capsule mechanical properties can be compromised by various factors such as prolonged exposure at high temperature and/or low pH and thus the leakage profile of a capsule with optimal mechanical properties can be compromised.

The time period for release of the content from an encapsulate may include a rapid or a burst release, a sustained release, a delayed release, and combinations thereof. Applicants have found that the satisfactory delivery of the content from an encapsulate may accomplished by incorporating photoresponsive elements into the polymer shell of the encapsulate. Particularly preferred photoresponsive elements include substituted azobenzene moieties. Without wishing to be bound by theory, it is thought that the absorption of light by the azobenzene moieties causes a rotation around the nitrogen-nitrogen double bond, resulting in a change in morphology of the polymer shell and a corresponding change in the release of the encapsulate. Depending on the substitution of the azobenzene, the wavelength of light required to trigger the release can be manipulated from near UV to visible. Furthermore, the azobenzene moieties may be incorporated into a wide range of polymers comprising the shell of an encapsulate as described in more detail below. Applicants have found that the specific properties of the polymers comprising the shell can have a profound influence on the stability of the encapsulate, including leakage, premature rupture, agglomeration, deposition and retention in a variety of cleaning compositions.

Applicants recognized that the source of the aforementioned leakage problem is not only due to the amount of water miscible and water immiscible monomers in the shell/wall of the encapsulate, but is also due to the low packing density of the molecules in the shell/wall of the encapsulate. The crosslink density in the shell/wall of the encapsulate also contributes to mechanical stability and leakage. Applicants recognized that the right balance of properties (stability in product and release during application) can be achieved by combining one or more water miscible monomers and one or more water immiscible monomers. Such encapsulates and compositions comprising such encapsulates are disclosed below.

In one aspect, An encapsulate comprising a shell comprising a polymer and a core, said shell encapsulating said core and comprising an electromagnetic radiation sensitive moiety that is sensitive to a species of electromagnetic radiation selected from the group consisting of infrared radiation, visible light, ultraviolet radiation and mixtures thereof, said core comprising a material selected from the group consisting of a perfume, a silicone, a biocontrol agent, an antimicrobial, a flavor, a heating or cooling agent, a drug, a sun screen and mixtures thereof is disclosed.

In one aspect, said electromagnetic radiation sensitive moiety comprises a substituted or unsubstituted azobenzene moiety.

In one aspect, said electromagnetic radiation sensitive moiety is provided by a monomer selected from the group consisting of monomers having the following structure:

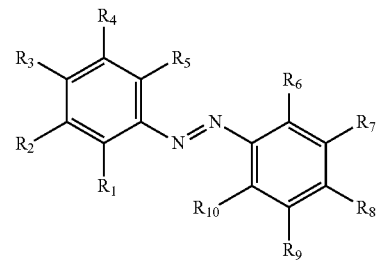

$R_1$, $R_2$, $R_3$, $R_4$, $R_5$, $R_6$, $R_7$, $R_8$, $R_9$ and $R_{10}$ are independently selected from the group consisting of

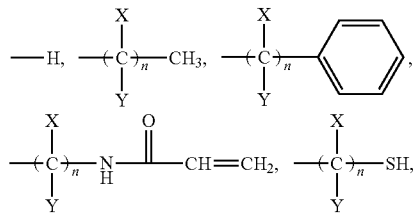

-continued
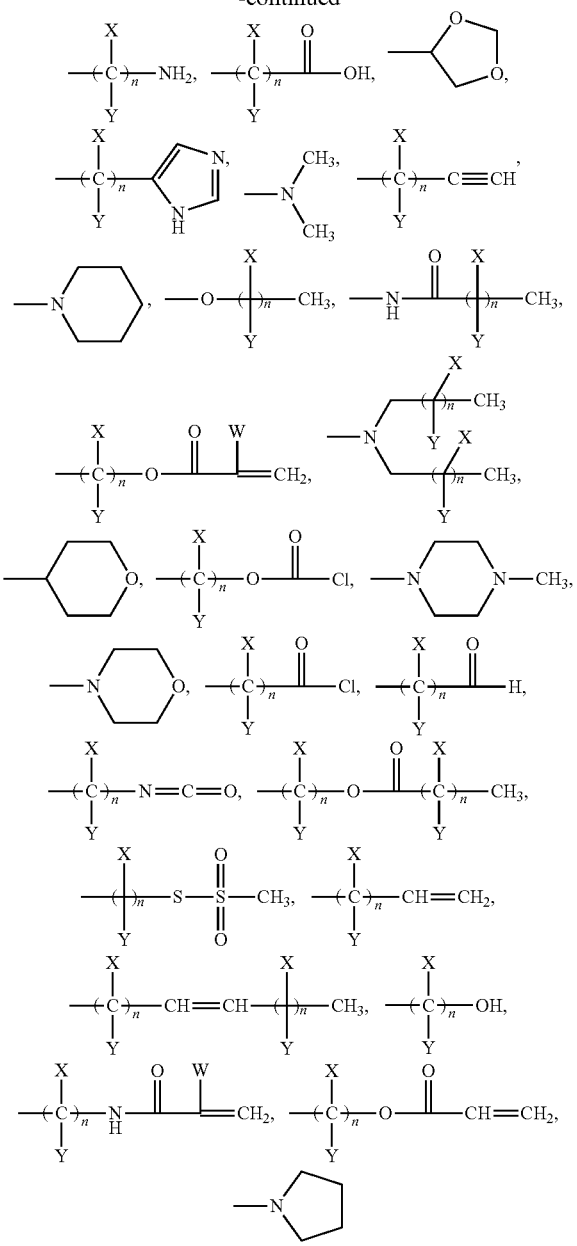
wherein n is an integer from 0 to 20 and X, Y and W can be independently selected from the group consisting of:
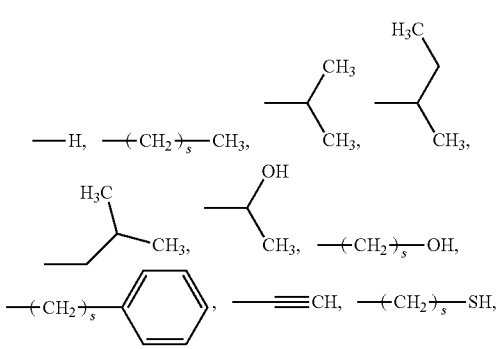
-continued
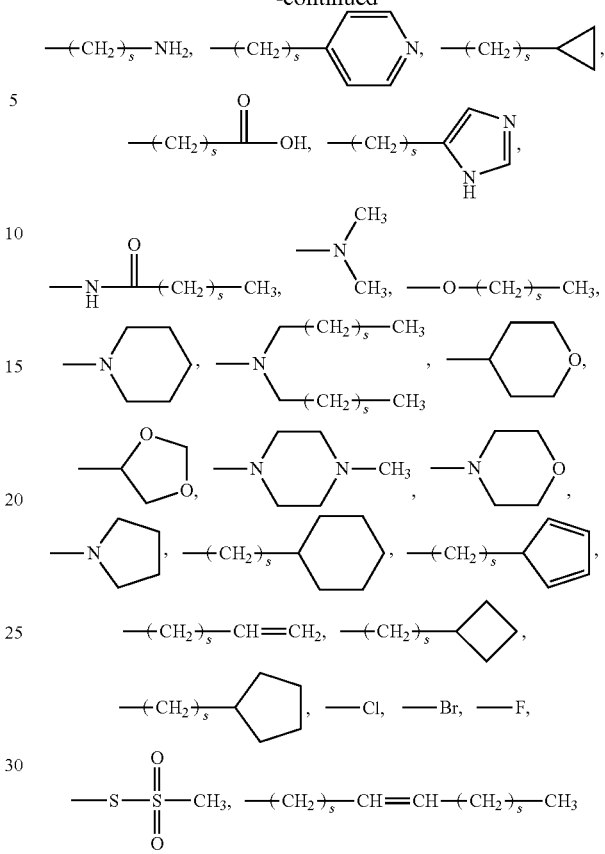
wherein s is an integer from 0 to 20 and at least 1 of $R_1$, $R_2$, $R_3$, $R_4$ and $R_5$ and 1 of $R_6$, $R_7$, $R_8$, $R_9$ and $R_{10}$ are selected from the group consisting of
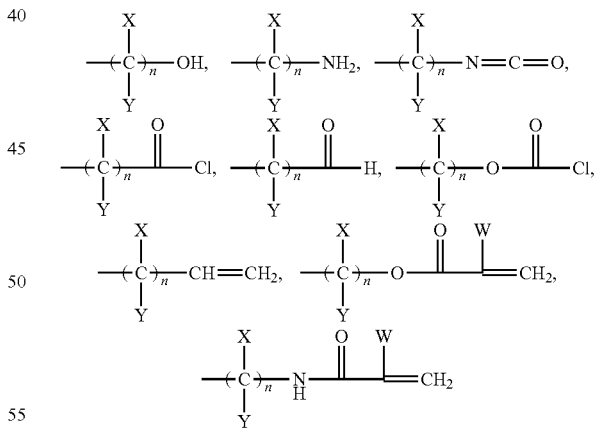
and mixtures thereof.
In one aspect, $R_3$ and $R_8$ are selected from the group consisting of
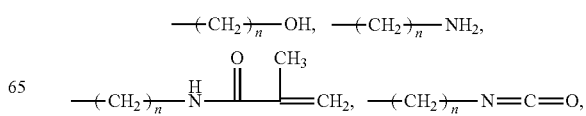

-continued

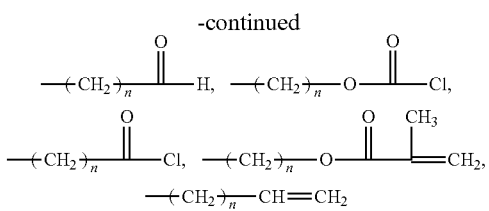

wherein n is an integer from 0 to 20 and $R_1$, $R_2$, $R_4$, $R_5$, $R_6$, $R_7$, $R_9$, $R_{10}$ are hydrogen (—H).

In one aspect, n is 0 or 1.

In one aspect, $R_3$ and $R_8$ are selected from the group consisting of

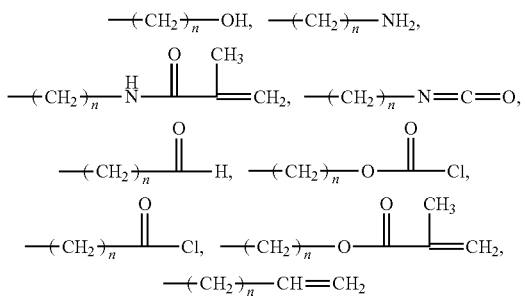

wherein n is an integer from 0 to 20 and $R_1$, $R_2$, $R_4$, $R_7$, $R_9$, $R_6$ are hydrogens (—H) and $R_5$ and $R_{10}$ are selected from the group consisting of

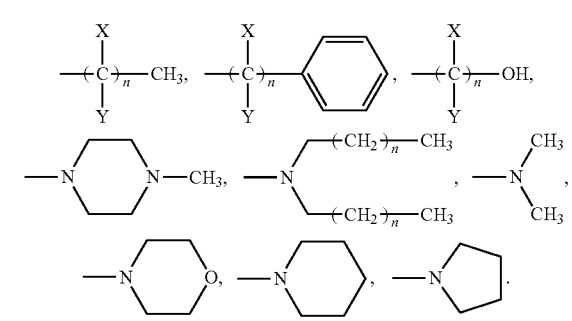

In one aspect, n is 0 or 1.

In one aspect, said monomer is selected from the group consisting of 4-[(E)-(4-chlorocarbonylphenyl)azo]benzoyl chloride, 4-[(E)-(4-aminophenyl)azo]aniline, [4-[(E)-[4-(aminomethyl)phenyl]azo]phenyl]methanamine, (E)-bis(4-vinylphenyl)diazene, [4-[(E)-[4-(hydroxymethyl)phenyl]azo]phenyl]methanol, 4-[(E)-(4-hydroxyphenyl)azo]phenol, 4-[(E)-[4-chlorocarbonyl-2-(diethylamino)phenyl]azo]-3-(diethylamino)benzoyl chloride, 4-[(E)-(4-chlorocarbonyl-2-pyrrolidin-1-yl-phenyl)azo]-3-pyrrolidin-1-yl-benzoyl chloride, 4-[(E)-(4-formylphenyl)azo]benzaldehyde, 4-[(E)-(4-chlorocarbonyl-2,6-dimethoxy-phenyl)azo]-3,5-dimethoxy-benzoyl chloride and mixtures thereof. Such monomers are detailed in Table 1 below.

TABLE 1 examples of monomers

4-[(E)-(4-chlorocarbonylphenyl)azo]benzoyl chloride

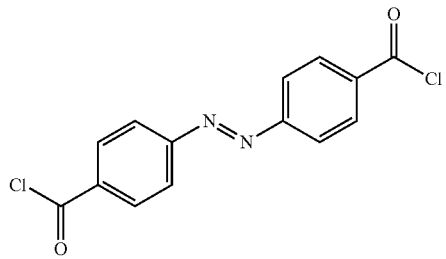 [SMILES: O=C(Cl)c1ccc(/N=N/c2ccc(C(=O)Cl)cc2)cc1]

4-[(E)-(4-aminophenyl)azo]aniline

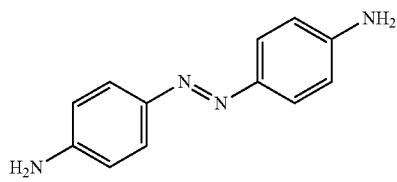 [SMILES: Nc1ccc(/N=N/c2ccc(N)cc2)cc1]

[4-[(E)-[4-(aminomethyl)phenyl]azo]phenyl]methanamine

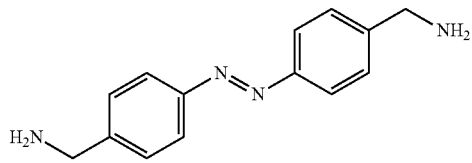 [SMILES: NCc1ccc(/N=N/c2ccc(CN)cc2)cc1]

(E)-bis(4-vinylphenyl)diazene

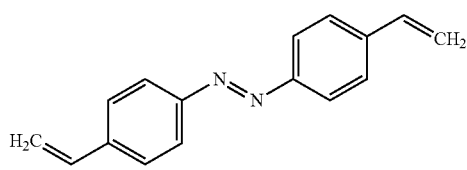 [SMILES: C=Cc1ccc(/N=N/c2ccc(C=C)cc2)cc1]

TABLE 1-continued

| examples of monomers | |
|---|---|
| 4-[(E)-(4-hydroxyphenyl)azo]phenol | |
| [4-[(E)-[4-(hydroxymethyl)phenyl]azo]phenyl]methanol | |
| 4-[(E)-(4-chlorocarbonyl-2-pyrrolidin-1-yl-phenyl)azo]-3-pyrrolidin-1-yl-benzoyl chloride | |
| 4-[(E)-(4-chlorocarbonyl-2,6-dimethoxy-phenyl)azo]-3,5-dimethoxy-benzoyl chloride | |
| 4-[(E)-[4-chlorocarbonyl-2-(diethylamino)phenyl]azo]-3-(diethylamino)benzoyl chloride | |
| 4-[(E)-(4-formylphenyl)azo]benzaldehyde | |

In one aspect, said encapsulate's shell comprises a material selected from the group consisting of polyamides, aminoplast polymers, polyurethanes, polyureas, polycarbonates, polyacrylates, polyesters and mixtures thereof.

In one aspect, said encapsulate's polymer comprises said electromagnetic radiation sensitive moiety.

In one aspect, said encapsulate's polymer comprises a main chain, said main chain comprising said electromagnetic radiation sensitive moiety.

In one aspect, said azobenzene moiety comprises an aldehyde functional group, an amine functional group, an alcohol functional group, an acyl chloride functional group, an acrylate functional group and mixtures thereof.

In one aspect, the azobenzene moiety is 4,4'-bis(chlorocarbonyl)azobenzene.

In one aspect, a composition comprising one or more encapsulates disclosed herein and an adjunct ingredient is disclosed.

In one aspect, said composition comprises, based on total composition weight from about 0.1% to about 25%, or from about 0.2% to about 15%, or even from about 0.4% to about 10% of said encapsulate.

In one aspect, said composition may comprise, in addition to the encapsulates that comprise an electromagnetic radiation sensitive moiety, encapsulates that do not comprise an electromagnetic radiation sensitive moiety. Such encapsulates that do not comprise an electromagnetic radiation sensitive moiety may be core shell encapsulates that may release their core material, which may be a benefit agent such as a perfume, due to the application of a stimuli, including but not limited to, pressure, heat, ionic strength, dehydration and/or diffusion.

In one aspect, said composition comprises:
a.) a population of encapsulates comprising from about 75% to about 100%, or from about 80% to about 100%, or even from about 85 to about 95% of an encapsulate comprising an azobenzene monomer substituted in the ortho position with one or more electron donor groups and in para with a cross-linking group such as 4-[(E)-(4-chlorocarbonyl-2-pyrrolidin-1-yl-phenyl)azo]-3-pyrrolidin-1-yl-benzoyl chloride, 4-[(E)-(4-chlorocarbonyl-2,6-dimethoxy-phenyl)azo]-3,5-dimethoxybenzoyl chloride and/or 4-[(E)-[4-chlorocarbonyl-2-(diethylamino)phenyl]azo]-3-(diethylamino)benzoyl chloride; and from about 0% to about 25%, or from about 0% to about 20% or even from about 5% to about 15% of an encapsulate comprising an azobenzene monomer substituted in the para position with 4-[(E)-(4-chlorocarbonylphenyl)azo]benzoyl chloride, 4-[(E)-(4-aminophenyl)azo]aniline and/or (E)-bis(4-vinylphenyl)diazene—such encapsulate selection provides fast core material release and thus is useful in compositions such as dish washing and/or scouring cleaners;
b.) a population of encapsulates comprising from about 25% to about 60%, or from about 30% to about 50%, or even from about 35% to about 45% of an encapsulate comprising an azobenzene monomer substituted in the ortho position with one or more electron donor groups and in para with a cross-linking group such as 4-[(E)-(4-chlorocarbonyl-2-pyrrolidin-1-yl-phenyl)azo]-3-pyrrolidin-1-yl-benzoyl chloride, 4-[(E)-(4-chlorocarbonyl-2,6-dimethoxy-phenyl)azo]-3,5-dimethoxybenzoyl chloride and/or 4-[(E)-[4-chlorocarbonyl-2-(diethylamino)phenyl]azo]-3-(diethylamino)benzoyl chloride; and from about 75% to about 40%, or from about 70% to about 50% or even from about 65% to about 55% of an encapsulate comprising an azobenzene monomer substituted in the para position with 4-[(E)-(4-chlorocarbonylphenyl)azo]benzoyl chloride, 4-[(E)-(4-aminophenyl)azo]aniline and/or (E)-bis(4-vinylphenyl)diazene—such encapsulate selection provides core material release over 3 to 6 hours and thus is useful in products such as sun creams and other body lotions);
c.) a population of encapsulates comprising from about 2% to about 20%, or from about 4% to about 18%, or even from about 5% to about 15% of an encapsulate comprising a polyamide shell having a ratio of electromagnetic radiation sensitive moiety to non-electromagnetic radiation sensitive moiety from about 95:5 to about 99:1, or from about 96:4 to about 98:2; and from about 80% to about 98%, from about 82% to about 96%, or even from about 85% to about 95% of an encapsulate comprising a polyamide shell having a ratio of electromagnetic radiation sensitive moiety to non-electromagnetic radiation sensitive moiety from about 87:13 to about 93:7, or from about 89:11 to about 91:9—such encapsulate selection provides core material release over 24 hours only during light exposure and thus is useful in products such as shampoos;
d.) a population of encapsulates comprising from about 0% to about 30%, or from about 2% to about 25%, or even from about 5% to about 22% of an encapsulate comprising a shell comprising from about 5% to about 50%, or from about 7% to about 47% or even from about 10% to about 45% of non-electromagnetic radiation sensitive moiety cross-linked with a substituted or unsubstituted moiety comprising from about 4 to about 10 carbons, or even from about 6 to about 8 carbons; and from about 70% to about 100%, or from about 75% to about 98%, or even from about 78% to about 95% of an encapsulate comprising a shell comprising a non-electromagnetic radiation sensitive moiety cross-linked with a substituted or unsubstituted moiety comprising from about 4 to about 10 carbons, or even from about 6 to about 8 carbons—such encapsulate selection provides core material release over 48 hours only during exposure to sun light and thus is useful in products such as hard surfaces;
e.) a population of encapsulates comprising from about 70% to about 100%, from about 75% to about 100%, or even from about 80% to about 95% of an encapsulate comprising a polyacrylic shell having a ratio of electromagnetic radiation sensitive moiety to non-electromagnetic radiation sensitive moiety from about 10:90 to about 95:5, or from about 15:85 to about 85:15, or even from about 20:80 to about 80:20; from about 0% to about 30%, and from about 0% to about 25%, or even from about 5% to about 20% of an encapsulate comprising a polyamide shell having a ratio of electromagnetic radiation sensitive moiety to non-electromagnetic radiation sensitive moiety from about 85:15 to about 90:10, or from about 86:14 to about 89:11—such encapsulate selection provides core material release over 48 hours and thus is useful in products such as body washes; and/or
f.) said composition's population of encapsulates comprising from about 70% to about 100%, from about 75% to about 100%, or even from about 80% to about 95% of an encapsulate comprising an aminoplast shell having a ratio of electromagnetic radiation sensitive moiety to non-electromagnetic radiation sensitive moiety from about 10:90 to about 95:5, or from about 15:85 to about 85:15, or even from about 20: 80 to about 80:20; and from about 0% to about 30%, from about 0% to about 25%, or even from about 5% to about 20% of an encapsulate comprising a polyamide shell having a ratio of electromagnetic radiation sensitive moiety to non-electromagnetic radiation sensitive moiety from about 85:15 to about 90:10, or from about 86:14 to about 89:11—such encapsulate selection is useful in products such as fabrics.

In one aspect disclosed herein, a population of encapsulates includes, for example at least 80%, at least 85%, or even at least 90% of the encapsulates, comprising a shell and a core, said shell comprising a cross-linked polymer comprising azobenzene moieties that form a wall that encapsulates said core, said core comprising a benefit agent. In some applications, it may be desirable to incorporate a population of encapsulates that releases its contents upon application of a suitable mechanical force together, with a population of encapsulates that releases its content upon exposure to light. The benefit agent within such encapsulates may be the same or different, depending on the application.

In one aspect, the benefit agent comprises a perfume composition, said perfume composition comprising perfume raw materials having a cLogP of from about 2 to about 5, or from about 2 to about 4.5, or even from about 2.5 to about 4.25.

In one aspect of said encapsulate, the encapsulate's core may comprise a perfume composition selected from the group consisting of:
- a) a perfume composition having a cLog P of less than about 5 to about 2, less than about 4.5 to about 2, less than about 4.25 to about 2.2, less than about 4.0 to about 2.5 or even less than about 3.75 to about 2.6;
- b) a perfume composition comprising, based on total perfume composition weight, at least about 60% or even at least about 70% perfume materials having a cLog P of less than about 5 to about 2, less than about 4.0 to about 2.0;
- c) a perfume composition comprising, based on total perfume composition weight, at least about 35%, at least about 50% or even at least about 60% perfume materials having a cLog P of less than about 4 to about 2, less than about 3.5 to about 2;
- d) a perfume composition comprising, based on total perfume composition weight, at least about 40% perfume materials having a cLog P of less than about 5 to about 2, less than about 4.0 to about 2 or even less than about 3.5 to about 2.0 and at least 1% perfume materials having a cLog P of less than 2.0 to about 1.0;
- e) a perfume composition comprising, based on total perfume composition weight, at least about 40% perfume materials having a cLog P of less than about 5 to about 2, less than about 4 to about 2 or even less than about 3.5 to about 2.0 and at least about 15% perfume materials having a cLog P of less than about 3.5 to about 1.5 or less than about 3.0 to about 1.5;
- f) a perfume composition comprising, based on total perfume composition weight, at least about 1% or even at least about 2.0% of a butanoate ester and at least about 1% of a pentanoate ester;
- g) a perfume composition comprising, based on total perfume composition weight, at least about 2.0% or even at least about 3.0% of an ester comprising an allyl moiety and at least about 10%, at least about 25% or even at least about 30% of another perfume comprising an ester moiety;
- h) a perfume composition comprising, based on total perfume composition weight, at least about 1.0% or even at least about 5.0% of an aldehyde comprising an alkyl chain moiety;
- i) a perfume composition comprising, based on total perfume composition weight, at least about 2.0% of a butanoate ester;
- j) a perfume composition comprising, based on total perfume composition weight, at least about 1.0% of a pentanoate ester;
- k) a perfume composition comprising, based on total perfume composition weight, at least about 3.0% of an ester comprising an allyl moiety and at least about 1.0% of an aldehyde comprising an alkyl chain moiety;
- l) a perfume composition comprising, based on total perfume composition weight, at least about 25% of a perfume comprising an ester moiety and at least about 1.0% of an aldehyde comprising an alkyl chain moiety; and
- m) a perfume composition comprising, based on total perfume composition on weight, from about 0.5% to about 50%, from about 1.0% to about 40%, or even from about 5.0% to about 30% of a parametric balancing agent.

with the proviso that the perfume composition does not contain or has less than 10% based on total perfume composition's weight of perfume materials containing the same functional groups than the monomers used for their encapsulation.

In another aspect, the benefit agent comprises silicone, antibacterial agents, flavors, heating or cooling agents. Other suitable benefit agents include flavor ingredients including spices or flavor enhancers that contribute to the overall flavor perception of the product into which the benefit agent delivery system is incorporated. Pharmaceutical benefit agents may include drugs. In one embodiment, a therapeutically acceptable amount of drug is employed.

In another aspect, biocontrol agents including biocides, antimicrobials, bactericides, fungicides, algaecides, mildewcides, disinfectants, sanitizer-like bleaches, antiseptics, insecticides, insect and/or moth repellant, vermicides, plant growth hormones, and the like are employed. In another aspect, antimicrobials including glutaraldehyde, cinnamaldehyde, and mixtures thereof are employed. In another aspect, azole antimicrobials may be employed as the benefit agent, wherein such azole antimicrobials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof.

In another aspect, typical insect and/or moth repellants such as citronellal, citral, N,N diethyl meta toluamide, Rotundial, 8-acetoxycarvotanacenone, and mixtures thereof may be employed. Other examples of insect and/or moth repellant for use as benefit agents herein are disclosed in U.S. Pat. Nos. 4,449,987, 4,693,890, 4,696,676, 4,933,371, 5,030,660, 5,196,200, and "Semio Activity of Flavor and Fragrance molecules on various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35-48. These publications are incorporated herein by reference.

In one aspect, said azobenzene moieties are found in the main chain of said cross-linked polyamide polymer. In another aspect, said azobenzene moieties are found in the cross-linking units.

In one aspect of said encapsulate, said cross-linked polymers may comprise polyamides, aminoplast polymers, polyurethanes, polyureas, polycarboantes, polyacrylates, polyesters and mixtures thereof.

In one aspect of said encapsulate, said polyamide, polyurethane, polyurea, polycarboante, polyester cross-linked polymers may comprise at least one water miscible and one water immiscible organic monomer.

In one aspect of said encapsulate, said cross-linked polymer comprising azobenzene moieties may comprise at least one water miscible monomer and one water immiscible organic monomer.

In one aspect of said encapsulate, said water miscible monomer may comprise a material selected from the group consisting of an aliphatic di- or triamine, an aromatic di- or triamine, an aliphatic di- or triol, an aromatic di- or triol and mixtures thereof. In one aspect, said diamines may be selected from the group consisting of 1,6-diaminohexane, 1,8-diaminooctane, ethylene diamine, phenylene diamine, substituted phenylene diamines, diaminopyridine, substituted diaminopyridines, diaminopyrazole, substituted diaminopyrazoles, and mixtures thereof. In one aspect, sadi triamines may be selected from the group consisting of diethylene triamine, melamine, and mixtures thereof. In one aspect, such diol may comprise ethylene glycol, 1,2-propanediol, 1,3-propanediol, 1-propen-1,3-diol, 1,4-butanediol, 1,3-butanodiol, 1,2-butanediol, 3-butene-1,2-diol, 3-butene-1,4-diol, 1,5-pentanediol, 1-penten-1,5-diol, 1,6-hexanediol, 3,4-dihydroxy-3-cyclobutene-1,2-dione, 5-hydroxy-2-(hydroxymethyl)-4H-pyran-4-one, (2E)-2,3-dihydroxy-2-butenedioic acid hydrate, 2,3,5,6-tetrahydroxybenzo-1,4-quinone, 4,4-dimethyl-1,2-cyclopentanediol, 3-methyl-1,3,5-pentanetriol, 3-methyl-1,5-pentanediol, (1S,2S)-1,2-cyclopentanediol, 1,3-cyclohexanediol, 1,5-hexanediol, 1,2,6-hexanetriol, 1,2,4-butanetriol and mixtures thereof. In one aspect, such triols may comprise glycerol, benzenetriol and mixtures thereof.

In one aspect of said encapsulate, said water immiscible organic monomer may be selected from the group consisting of diacyl chlorides, triacyl chlorides, diisocyanates, bischloroformates and mixtures thereof. In one aspect, said diacyl chlorides may be selected from the group consisting of terephthaloyl chloride, 4,4'-bis(chlorocarbonyl)azobenzene, sebacoyl dichloride, adipoyl dichloride, and mixtures thereof and said triacyl chlorides may be selected from the group consisting of trimesoyl chloride, 1,3,5-benzentricarbonyl chloride, and mixtures thereof. In one aspect, such diisocyanates may comprise 1-isocianato-4-[(4-fenilisocianato)metil]benzene, 2,4-diisocyanato-1-methyl-benzene, 1,6-diisocyanatohexane, 5-isocyanato-1-(isocyanatomethyl)-1,3,3-trimethyl-cyclohexane and mixtures thereof. In one aspect, such bischloroformates may comprise bisphenol A bis(chloroformate), bisphenol Z bis(chloroformate) and mixtures thereof.

In one aspect of said encapsulate, said water miscible monomer may contain the azobenzene moiety.

In one aspect of said encapsulate, said water immiscible organic monomer may contain the azobenzene moiety.

Applicants have recognized that for some exemplary applications, the mild reaction conditions of a condensation polymerization between a di- or triamine and a di- or triacyl chloride containing azobenzene moieties may be particularly preferred. For other applications, the incorporation of azobenzene moieties under free radical polymerization conditions may be advantageous. In still other applications, a substituted azobenzene containing one or more aldehyde groups or one or more alcohol groups or one or more amine groups can be incorporated into melamine formaldehyde, polyurethane, polyester, polyurea and/or polycarbonate shells. In still other applications, a substituted azobenzene containing one or more acrylate groups can be incorporated into polyacrylate shells.

In one aspect of said encapsulate, said cross-linked polyamide polymer comprising azobenzene moieties may comprise a crosslinking agent selected from the group consisting of a multifunctional di- or triamine, a multifunctional di- or triacyl chloride, and mixtures thereof. In one aspect, said multifunctional di- or triamines may be selected from melamine. In one aspect, said multifunctional acyl chlorides may be selected from the group consisting of 1,2,3,4-cyclopentane tetracarboxylic acid chloride, 1,3,5-pentanetricarbonyl chloride and mixtures thereof. In still another aspect, other types of multifunctional reactive crosslinkers may be used. A nonlimiting example of this type of cross-linker includes cyanuric chloride.

In one aspect of said encapsulate, said cross-linked polymer comprising azobenzene moieties may comprise two or more water miscible monomers.

In one aspect of said encapsulate, said cross-linked polymer comprising azobenzene moieties may comprise two or more water immiscible organic monomers.

In one aspect of said encapsulate, the azobenzene moieties may be incorporated into the main chain of polymers comprising the shell of the encapsulate via condensation reaction between an azobenzene diacyl chloride and a diamine. In another aspect of said encapsulate, the azobenzene moieties may be incorporated into polymer chains comprising the shell of the encapsulate via free radical polymerization.

In one aspect of said encapsulate, a slight excess of the diamine relative to the di- or triacyl chloride or to the sum of the di- or tri-acyl chloride and multifunctional di- or tri-acyl chloride provides a beneficial effect on the longevity of fragrance release. In another aspect of said encapsulate, incorporating a small amount of amine-functional monomer into the shell of encapsulates comprising polymers prepared by free radical polymerization provides a beneficial effect on the longevity of fragrance release. Without wishing to be bound by theory, it is believed that the positive charge imparted by the amine functional group in the shell of said encapsulate can further beneficially improve deposition and retention on surfaces of interest, which are often slightly negative in charge.

In one aspect, said azobenzene moieties are found in the cross-linking units of free radically polymerizable monomers.

In one aspect of said encapsulate, said free radically polymerizable monomer structures may be selected from the group consisting of divinyl, distyryl, diacryloxy, diacrylamido, dimethacryloxy, dimethacrylamido vinyl, styryl, acryloxy, acrylamido, methacryloxy, methacrylamido and mixtures thereof. In one aspect, said distyryl may be selected from the group consisting of 4,4'-bis-vinyl-azobenzene. In another aspect, said diacryloxy may be selected from the group consisting of 4,4'-bis-methacryloxy-azobenzene, 2,2'-bis-styryl-azobenzene, 3,3'-bis-styryl-azobenzene, 2,4'-bis-styryl-azobenzene, 4,4'-bis-methacryloxy-azobenzene, 3,3'-bis-methacryloxy-azobenzene, 2,2'-bis-methacryloxy-azobenzene, 2,4'-bis-methacryloxy-azobenzene, 4,4'-bis-acryloxy-azobenzene, 3,3'-bis-acryloxy-azobenzene, 2,2'-bis-acryloxy-azobenzene, 2,4'-bis-acryloxy-azobenzene, 4,4'-bis-acrylamido-azobenzene, 3,3'-bis-acrylamido-azobenzene, 2,2'-bis-acrylamido-azobenzene, 2,4'-bis-acrylamido-azobenzene, 4,4'-bis-methacrylamido-azobenzene, 3,3'-bis-methacrylamido-azobenzene, 2,2'-bis-methacrylamido-azobenzene, 2,4'-bis-methacrylamido-azobenzene and mixtures thereof.

In one aspect, said azobenzene moieties are found in the cross-linking units of melamine-formaldehyde co-reactive monomers.

In one aspect of said encapsulate, the melamine-formaldehyde co-reactive monomer structures may be selected from the group consisting of diol, dialdehyde and diamine, alcohol, amine and aldehyde and mixtures thereof. In one aspect, said diamino may be selected from the group consisting of 4,4'-bis-amino-azobenzene. In another aspect, said diols may be selected from the group consisting of 4,4'-bis-hydroxymethyl-azobenzene, 2,2'-bis-hydroxymethyl-azobenzene, 3,3'-bis-hydroxymethyl-azobenzene and 1,3'-bis-hydroxymethyl-azobenzene In one aspect of said encapsulate, said encapsulate may have a leakage index of from about 0 to about 0.35, from about 0.02 to about 0.20, or even from about 0.05 to about 0.15.

In one aspect a composition, that may have any of the parameters disclosed herein and may comprise any of the encapsulates described herein and an adjunct material, is disclosed.

In one aspect a consumer product comprising, based on total consumer product weight, from about 0.01% to about 80%, from about 0.1% to about 50%, from about 1.0% to about 25% or from about 1.0% to about 10% of the encapsulates disclosed herein, is disclosed.

Suitable Perfume Raw Materials

Perfumes that provide improved perfume performance may comprise Perfume Raw Materials as given in Table 1 below.

TABLE 2

Useful Perfume Raw Materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | Cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | 21aphta lactone | 6-[(E)-pent-2-enyl]oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |

TABLE 2-continued

Useful Perfume Raw Materials

| Item | Common Name | IUPAC Name |
|---|---|---|
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | Cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | 22aphthalene-2-yl-phenylmethanone |
| 93 | decen-1-yl cyclopentanone | 2-[(2E)-3,7-dimethylocta-2,6-dienyl]cyclopentan-1-one |
| 94 | fruity cyclopentanone (veloutone) | 2,2,5-trimethyl-5-pentylcyclopentan-1-one |
| 96 | Grapefruit Mercaptan | 2-(4-methyl-1-cyclohex-3-enyl)propane-2-thiol |
| 97 | Buccoxime | N-(1,5-dimethyl-8-bicyclo[3.2.1]octanylidene)hydroxylamine |
| 98 | Labienoxime | 2,4,4,7-Tetramethyl-6,8-nonadiene-3-one oxime |
| 101 | Diethyl maleate | diethyl but-2-enedioate |
| 102 | Ethyl Acetoacetate | ethyl 3-oxobutanoate |
| 103 | Frutonile | 2-Methyldecanenitrile |
| 104 | Methyl dioxolan | ethyl 2-(2-methyl-1,3-dioxolan-2-yl)acetate |
| 105 | Cetalox | 3$^a$,6,6,9$^a$-tetramethyl-2,4,5,5$^a$,7,8,9,9b-octahydro-1H-benzo[e][1]benzofuran |
| 107 | Delta-damascone | (E)-1-(2,6,6-trimethyl-1-cyclohex-3-enyl)but-2-en-1-one |
| 109 | Flor acetate | |
| 110 | Ionone gamma methyl | (E)-3-methyl-4-(2,6,6-trimethyl-1-cyclohex-2-enyl)but-3-en-2-one |
| 113 | Violiff | [(4Z)-1-cyclooct-4-enyl] methyl carbonate |
| 114 | Cymal | 3-(4-propan-2-ylphenyl)butanal |
| 115 | Bourgeonal | 3-(4-tert-butylphenyl)propanal |
| 116 | Eucalyptol | 1,3,3-trimethyl-2-oxabicyclo[2,2,2]octane |
| 117 | Freskomenthe | 2-sec-butylcyclohexanone |

TABLE 2-continued

Useful Perfume Raw Materials

| Item | Common Name | IUPAC Name |
|---|---|---|
| 118 | Gyrane | 2H-Pyran, 6-butyl-3,6-dihydro-2,4-dimethyl- |
| 119 | Alpha-ionone | (E)-4-(2,6,6-trimethyl-1-cyclohex-2-enyl)but-3-en-2-one |
| 120 | Terpinyl acetate | (±)-2-(4-Methyl-3-cyclohexenyl)isopropyl acetate |
| 121 | Melonal | 2,6-Dimethyl-5-heptenal |
| 122 | Aphermate | 1-(3,3-dimethylcyclohexyl)ethyl formate |
| 123 | Dihydro myrcenol | 2,6-dimethyloct-7-en-2-ol |
| 124 | Bacdanol ® | 2-ethyl-4-(2,2,3-trimethyl-3-cyclo-penten-1-yl)-2-buten-1-ol |

Suitable Parametric Balancing Agents

In one aspect, the encapsulates disclosed herein may comprise a parametric balancing agent.

In one aspect, at least a portion of said parametric balancing agent is contained in said encapsulate's shell. In another aspect, said encapsulate's core may comprise at least a portion of said parametric balancing agent.

In one aspect, said parametric balancing agent may be a density balancing agent. Without being bound by theory, density balancing agents are materials that are able to balance the density of an encapsulate so that such encapsulate can be stably suspended in a fluid consumer good. In one aspect of said encapsulate, said encapsulate may have a settling velocity of less than about 1.5 cm/year, less than about 1.0 cm/year. In another aspect of said encapsulate, said perfume composition may comprise one or more fluids and may have a density such that the density ratio of said encapsulate and at least one of said one or more fluids is from about 0.9:1 to about 1.1:1. Suitable density balancing agents include: brominated vegetable oil, Tint Ayd PC 9003 and those listed in U.S. patent application Ser. No. 29/035,365 A1.

For example, the density balancing agents may be metal oxides selected from but not limited to titanium dioxide ($TiO_2$), zinc oxide (ZnO), $Fe_2O_3$, $CO_2O_3$, CoO, NiO, AgO, CuO, zicornium dioxide ($ZrO_2$), silica, and other metal oxides. They should have specific density of greater than unity. Oxides that can function both as densification agent and provide additional functional properties are particularly useful.

In one aspect, the density of the density balancing agent is greater than 1. By adding density balancing agents to the core, the density of the encapsulate can be independently adjusted to a desired level. Hydrophobically modified metal oxides are useful. Examples of metal oxides include, but are not limited to, Uvinul® TiO2, Z-COTE® HP1, T-lite™ SF. T-lite™ SF-S, T-lite™ MAX, and Z-COTE® MAX manufactured by BASF; Aerosil® R812, Aerosil® R972/R94 from Evonik; and Ti-Pure® R-700, and Ti-Select™ TS-6200 from Dupont.

The density balancing agents may also be selected from organic compounds including brominated vegetable oil (BVO) and sucrose acetate isobutyrate. Such density balancing agents are available from Eastman chemical (Kingsport, Tenn. 37662) under the trade name: Sustane SAIB, Sustane SAIB MCT, Sustane SAIB ET-10, Eastman SAIB-100, Eastman SAIB-90EA, and Eastman SAIB-90. For the purpose of densification, any substances that possesses a density of greater than 1 and does not significantly react with the fragrance may be used. Furthermore, a material that is odorless or does not interfere with the primary odor of the fragrance is particularly useful. The selection can be made based on the chemical and physical compatibility of the densification agent and that of the fragrance core.

The density balancing agents may also be selected from inert metallic particles or metallic compounds or metallic alloys since these materials normally posses density of greater than 1.0 and can be highly effective in providing the desired density. Examples are silver (Ag), zinc (Zn), iron (Fe), cobalt (Co), Nickel (Ni), and copper (Cu). Useful materials are those compatible with the fragrance core.

In the case of a solid density balancing agent, the material can be of any physical dimension and morphology compatible with the desired encapsulate characteristics (e.g., size). The core materials can be selected from materials with dimensions ranging from a few nanometers to microns. As far as the physical dimension is concerned, the upper and lower limit of the core densification agent will be ultimately determined by the physical dimension of the encapsulates. For example, if one is to prepare a 30 micron densified capsule, the maximum physical dimension of the densification agent is limited to 30 micron or less. It is possible that, for optimal performance, there might exist a relationship between the physical dimension of the capsule and that of the core densification agent. For example, a larger capsule may need a densification agent with a larger physical size for better breakage and release. This may be explainable if the capsules breakage is by protrusion force. Likewise, a smaller capsule may benefit from material with a smaller grain size.

The core materials may further be hollow, porous, mesoporous, nano-porous or completely filled. The core materials can also be of any regular or irregular shape including sphere, square, needles, fibers, and ellipsoids. The physical dimension of the core materials can range from nanoscaled to micro-sized materials. The densification agents in the core can have any dimension, as long as they can be encapsulated in the polyamide encapsulating shell and as long as the fragrance core remains liquid after the fragrance core is mixed with the densification agent.

Additional suitable density balancing agents include those listed in Table 3 below.

TABLE 3

Density Balancing Agents Useful For Balancing Encapsulates Having Cores With a Density of Less Than 1

| Item | CAS Number | Registry Name | Trade name | Specific Gravity 25° C. (g/cm$^3$) |
|---|---|---|---|---|
| 1 | 116-66-5 | 1h-indene, 2,3-dihydro-1,1,3,3,5-pentamethyl-4,6-dinitro- | moskene | solid |
| 3 | 120-24-1 | benzeneacetic acid, 2-methoxy-4-(1-propenyl)phenyl ester | isoeugenyl phenylacetate | solid |
| 4 | 2530-10-1 | ethanone, 1-(2,5-dimethyl-3-thienyl)- | 3-acetyl-2,5-dimeththiiophene | 1.1783 |
| 5 | 16546-01-3 | oxiranecarboxylic acid, 3-(4-methoxyphenyl)-, ethyl ester | methoxy ethyl phenyl glycidate | solid |
| 6 | 144761-91-1 | benzoic acid, 2-[(1-hydroxy-3-phenylbutyl)amino]-, methyl ester | trifone | solid |
| 7 | 6951-08-2 | 1,3-benzodioxole-5-carboxylic acid, ethyl ester | ethyl piperonylate | 1.2430 |
| 9 | 100-09-4 | benzoic acid, 4-methoxy- | p-anisic acid | solid |
| 10 | 90-17-5 | benzenemethanol, .alpha.-(trichloromethyl)-, acetate | trichloromethyl phenyl carbinyl acetate | solid |
| 11 | 10031-96-6 | phenol, 2-methoxy-4-(2-propenyl)-, formate | eugenyl formate | solid |
| 12 | 531-26-0 | phenol, 2-methoxy-4-(2-propenyl)-, benzoate | eugenyl benzoate | solid |
| 13 | 5320-75-2 | 2-propen-1-ol, 3-phenyl-, benzoate | cinnamyl benzoate | solid |
| 14 | 122-27-0 | benzeneacetic acid, 3-methylphenyl ester | m-cresyl phenylacetate | solid |
| 15 | 145-39-1 | benzene, 1-(1,1-dimethylethyl)-3,4,5-trimethyl-2,6-dinitro- | musk tibetine | solid |
| 16 | 101-94-0 | benzeneacetic acid, 4-methylphenyl ester | p-tolyl phenylacetate | solid |
| 17 | 102-16-9 | benzeneacetic acid, phenylmethyl ester | benzyl phenylacetate | solid |
| 18 | 102-17-0 | benzeneacetic acid, (4-methoxyphenyl)methyl ester | anisyl phenylacetate | solid |
| 19 | 103-41-3 | 2-propenoic acid, 3-phenyl-, phenylmethyl ester | benzyl cinnamate | solid |
| 20 | 103-53-7 | 2-propenoic acid, 3-phenyl-, 2-phenylethyl ester | phenethyl cinnamate | solid |
| 21 | 10402-33-2 | benzeneacetic acid, 2-methoxy-4-(2-propenyl)phenyl ester | eugenyl phenylacetate | solid |
| 23 | 111753-60-7 | benzoic acid, 2-[[3-(1,3-benzodioxol-5-yl)-2-methylpropylidene]amino]-, methyl ester | corps oranger 2 | solid |
| 25 | 1132-21-4 | benzoic acid, 3,5-dimethoxy- | 3,5-dimethoxybenzoic acid | solid |
| 26 | 118-55-8 | benzoic acid, 2-hydroxy-, phenyl ester | phenyl salicylate | solid |
| 27 | 118-58-1 | benzoic acid, 2-hydroxy-, phenylmethyl ester | benzyl salicylate | solid |
| 28 | 118-61-6 | benzoic acid, 2-hydroxy-, ethyl ester | ethyl salicylate | solid |
| 29 | 119-36-8 | benzoic acid, 2-hydroxy-, methyl ester | methyl salicylate | solid |
| 30 | 134-20-3 | benzoic acid, 2-amino-, methyl ester | methyl anthranilate | 1.1873 |
| 31 | 119-53-9 | ethanone, 2-hydroxy-1,2-diphenyl- | benzoin | solid |
| 32 | 120-47-8 | benzoic acid, 4-hydroxy-, ethyl ester | ethyl 4-hydroxybenzoate | solid |
| 33 | 120-51-4 | benzoic acid, phenylmethyl ester | benzyl benzoate | 1.1308 |
| 35 | 120-75-2 | benzothiazole, 2-methyl- | 2-methylbenzothiazole | solid |
| 36 | 1210-35-1 | 5h-dibenzo[a,d]cyclohepten-5-one, 10,11-dihydro- | dibenzosuberenone | solid |
| 37 | 121-39-1 | oxiranecarboxylic acid, 3-phenyl-, ethyl ester | ethyl 3-phenylglycidate | solid |
| 38 | 121-98-2 | benzoic acid, 4-methoxy-, methyl ester | methyl p-anisate | solid |
| 39 | 122-69-0 | 2-propenoic acid, 3-phenyl-, 3-phenyl-2-propenyl ester | cinnamyl cinnamate | 1.1210 |
| 40 | 122760-84-3 | tricyclo[3.3.1.13,7]decan-2-ol, 4-methyl-8-methylene- | tricyclo[3.3.1.13,7]decan-2-ol, 4-methyl-8-methylene- | solid |
| 41 | 122760-85-4 | tricyclo[3.3.1.13,7]decan-2-ol, 4-methyl-8-methylene-, acetate | tricyclo[3.3.1.13,7]decan-2-ol, 4-methyl-8-methylene-, acetate | solid |
| 42 | 131-55-5 | methanone, bis(2,4-dihydroxyphenyl)- | benzophenone-2 | solid |
| 43 | 131-57-7 | methanone, (2-hydroxy-4-methoxyphenyl)phenyl- | oxybenzone | solid |
| 44 | 132-64-9 | Dibenzofuran | 2,2'-biphenylene oxide | solid |
| 45 | 133-18-6 | benzoic acid, 2-amino-, 2-phenylethyl ester | phenethyl anthranilate | 1.1752 |
| 46 | 1333-52-4 | ethanone, 1-(naphthalenyl)- | 1-(naphthyl)ethan-1-one | solid |
| 47 | 13678-67-6 | furan, 2,2'-[thiobis(methylene)]bis- | 2,2'-(thiodimethylene)-difuran | solid |
| 48 | 139-45-7 | 1,2,3-propanetriol, tripropanoate | glyceryl tripropanoate | 1.1009 |
| 49 | 140-10-3 | 2-propenoic acid, 3-phenyl-, (e)- | trans-cinnamic acid | solid |

TABLE 3-continued

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 51 | 14173-25-2 | disulfide, methyl phenyl | methyl phenyl disulfide | 1.1776 |
| 53 | 14737-91-8 | 2-propenoic acid, 3-(2-methoxyphenyl)-, (z)- | cis-2-methoxycinnamic acid | solid |
| 54 | 148-24-3 | 8-quinolinol | 8-hydroxyquinoline | solid |
| 55 | 150-60-7 | disulfide, bis(phenylmethyl) | dibenzyl disulfide | solid |
| 56 | 19224-26-1 | 1,2-propanediol, dibenzoate | propylene glycol dibenzoate | 1.1686 |
| 57 | 2039-82-9 | benzene, 1-bromo-4-ethenyl- | 4-bromostyrene | 1.3931 |
| 58 | 2050-87-5 | trisulfide, di-2-propenyl | diallyl trisulfide | 1.1346 |
| 60 | 2257-09-2 | benzene, (2-isothiocyanatoethyl)- | phenethyl isothiocyanate | solid |
| 61 | 22717-57-3 | benzoic acid, 2-hydroxy-5-methyl-, methyl ester | methyl-5-methylsalicylate | solid |
| 62 | 23654-92-4 | 1,2,4-trithiolane, 3,5-dimethyl- | 3,5-dimethyl-1,2,4-trithiolane | 1.3018 |
| 63 | 23747-43-5 | propanoic acid, 2-(methyldithio)-, ethyl ester | ethyl 2-(methyldithio)propionate | 1.1378 |
| 64 | 25485-88-5 | benzoic acid, 2-hydroxy-, cyclohexyl ester | cyclohexyl salicylate | solid |
| 65 | 25628-84-6 | benzoic acid, 2[(1-oxopropyl)amino]-, methyl ester | anthranilic acid, n-propionyl-, methyl ester | solid |
| 66 | 26486-14-6 | ethanethioic acid, s-(4,5-dihydro-2-methyl-3-furanyl) ester | 2-methyl-3-thioacetoxy-4,5-dihydrofuran | solid |
| 67 | 2719-08-6 | benzoic acid, 2-(acetylamino)-, methyl ester | n-acetyl methyl anthranilate | solid |
| 68 | 2765-04-0 | 1,3,5-trithiane, 2,4,6-trimethyl- | 2,4,6-trimethyl-1,3,5-trithiane | solid |
| 69 | 30954-98-4 | benzoic acid, 2-amino-, propyl ester | propyl anthranilate | solid |
| 70 | 3121-70-8 | butanoic acid, 1-naphthalenyl ester | alpha-naphthyl butyrate | solid |
| 71 | 33662-58-7 | benzoic acid, 2,4-dihydroxy-3-methyl-, methyl ester | methyl 3-methylresorcylate | solid |
| 72 | 34135-85-8 | trisulfide, methyl 2-propenyl | allyl methyl trisulfide | 1.1884 |
| 73 | 34171-46-5 | 2-furanmethanol, benzoate | furfuryl benzoate | solid |
| 74 | 34265-58-2 | benzoic acid, 2-hydroxy-5-methyl-, ethyl ester | ethyl-5-methylsalicylate | solid |
| 75 | 3591-42-2 | benzene, (2,2-dichloro-1-methylcyclopropyl)- | 1,1-dichloro-2-methyl-2-phenylcyclopropane | solid |
| 76 | 36880-33-8 | 2-thiophenecarboxaldehyde, 5-ethyl- | 5-ethyl-2-thiophenecarbaldehyde | solid |
| 77 | 37837-44-8 | benzoic acid, [(phenylmethylene)amino]-, methyl ester | methyl n-benzylidene-2-aminobenzoate | solid |
| 78 | 38325-25-6 | spiro[1,3-dithiolo[4,5-b]furan-2,3'(2'h)-furan], hexahydro-2',3a-dimethyl- | spiro(2,4-dithia-1-methyl-8-oxabicyclo[3.3.0]octane-3,3') | solid |
| 79 | 40527-42-2 | 1,3-benzodioxole, 5-(diethoxymethyl)- | heliotropine diethyl acetal | solid |
| 80 | 40785-62-4 | cyclododeca[c]furan, 1,3,3a,4,5,6,7,8,9,10,11,13a-dodecahydro- | 14-oxabicyclo[10.3.0]-2-pentadecene | solid |
| 81 | 4112-89-4 | benzeneacetic acid, 2-methoxyphenyl ester | guaiacyl phenylacetate | solid |
| 82 | 4265-16-1 | 2-benzofurancarboxaldehyde | 2-benzofurancarboxaldehyde | solid |
| 83 | 43040-01-3 | 1,2,4-trithiane, 3-methyl- | 3-methyl-1,2,4-trithiane | solid |
| 84 | 4437-20-1 | furan, 2,2'-[dithiobis(methylene)]bis- | 2,2'-(dithiomethylene)difuran | 1.3144 |
| 85 | 458-37-7 | 1,6-heptadiene-3,5-dione, 1,7-bis(4-hydroxy-3-methoxyphenyl)-, (e,e)- | curcumin | solid |
| 86 | 4707-47-5 | benzoic acid, 2,4-dihydroxy-3,6-dimethyl-, methyl ester | methyl 2,4-dihydroxy-3,6-dimethylbenzoate | solid |
| 87 | 5446-02-6 | benzoic acid, 2-hydroxy-4-methoxy-, methyl ester | methyl 4-methoxysalicylate | solid |
| 88 | 5461-08-5 | propanoic acid, 2-methyl-, 1,3-benzodioxol-5-ylmethyl ester | piperonyl isobutyrate | solid |
| 89 | 54644-28-9 | 1,2,4-trithiolane, 3,5-diethyl- | 3,5-diethyl-1,2,4-trithiolane | solid |
| 90 | 54934-99-5 | 1,2,4-trithiolane, 3,5-bis(1-methylethyl)- | 3,5-diisopropyl-1,2,4-trithiolane | solid |
| 91 | 57500-00-2 | furan, 2-[(methyldithio)methyl]- | methyl furfuryl disulfide | 1.2240 |
| 92 | 5756-24-1 | tetrasulfide, dimethyl | dimethyl tetrasulfide | 1.4180 |

TABLE 3-continued

Density Balancing Agents Useful For Balancing Encapsulates Having Cores With a Density of Less Than 1

| Item | CAS Number | Registry Name | Trade name | Specific Gravity 25° C. (g/cm$^3$) |
|---|---|---|---|---|
| 93 | 57568-60-2 | benzene acetaldehyde, .alpha.-(2-furanylmethylene)- | 2-phenyl-3-(2-furyl)prop-2-enal | solid |
| 94 | 586-38-9 | benzoic acid, 3-methoxy- | 3-methoxybenzoic acid | solid |
| 95 | 5925-68-8 | benzenecarbothioic acid, s-methyl ester | s-ethyl benzothioate | 1.1179 |
| 96 | 606-45-1 | benzoic acid, 2-methoxy-, methyl ester | methyl o-methoxybenzoate | 1.1331 |
| 97 | 607-88-5 | benzoic acid, 2-hydroxy-, 4-methylphenyl ester | p-cresyl salicylate | solid |
| 98 | 607-90-9 | benzoic acid, 2-hydroxy-, propyl ester | propyl salicylate | solid |
| 99 | 6099-03-2 | 2-propenoic acid, 3-(2-methoxyphenyl)- | 2-methoxycinnamic acid | solid |
| 100 | 6099-04-3 | 2-propenoic acid, 3-(3-methoxyphenyl)- | 3-methoxycinnamic acid | solid |
| 101 | 6110-36-7 | benzoic acid, 2-hydroxy-4-methoxy-6-methyl-, ethyl ester | 2-hydroxy-4-methoxy-6-methylbenzoic acid, ethyl ester | solid |
| 102 | 613-84-3 | benzaldehyde, 2-hydroxy-5-methyl- | 5-methyl salicylic aldehyde | solid |
| 103 | 614-33-5 | 1,2,3-propanetriol, tribenzoate | glyceryl tribenzoate | solid |
| 104 | 614-34-6 | benzoic acid, 4-methylphenyl ester | p-cresyl benzoate | solid |
| 105 | 615-10-1 | 2-furancarboxylic acid, propyl ester | propyl 2-furoate | 1.1128 |
| 106 | 617-01-6 | benzoic acid, 2-hydroxy-, 2-methylphenyl ester | o-tolyl salicylate | solid |
| 107 | 617-05-0 | benzoic acid, 4-hydroxy-3-methoxy-, ethyl ester | ethyl vanillate | solid |
| 108 | 621-82-9 | 2-propenoic acid, 3-phenyl- | cinnamic acid | solid |
| 109 | 62265-99-0 | benzene, 1,3-dibromo-2-methoxy-4-methyl-5-nitro- | 1,3-dibromo-2-methoxy-4-methyl-5-nitrobenzene | solid |
| 110 | 622-78-6 | benzene, (isothiocyanatomethyl)- | benzyl isothiocyanate | 1.2200 |
| 111 | 623-20-1 | 2-propenoic acid, 3-(2-furanyl)-, ethyl ester | ethyl 3-(2-furyl)-acrylate | 1.1304 |
| 112 | 6258-60-2 | benzenemethanethiol, 4-methoxy- | p-methoxy benzyl mercaptan | 1.1108 |
| 113 | 6258-63-5 | 2-thiophenemethanethiol | thenyl mercaptan | 1.1871 |
| 114 | 65416-19-5 | benzene, 1,1'-[(2-phenylethylidene)bis(oxymethylene)]bis- | phenylacetaldehyde dibenzyl acetal | solid |
| 117 | 67801-43-8 | benzenepropanoic acid, .beta.-oxo-, 4-methylphenyl ester | p-tolyl 3-oxo-3-phenylpropionate | solid |
| 118 | 67860-00-8 | 1h-indole-3-heptanol, .eta.-1h-indol-3-yl-.alpha.,.alpha.,.epsilon.-trimethyl- | indolene | solid |
| 119 | 68555-58-8 | benzoic acid, 2-hydroxy-, 3-methyl-2-butenyl ester | prenyl salicylate | solid |
| 120 | 68844-96-2 | 1,3-benzodioxole-5-propanol, .alpha.-methyl-, acetate | alpha-methyl-1,3-benzodioxole-5-propanol, acetate | solid |
| 121 | 6911-51-9 | thiophene, 2,2'-dithiobis- | 2-thienyl disulfide | solid |
| 122 | 69-72-7 | benzoic acid, 2-hydroxy- | salicylic acid | solid |
| 123 | 698-27-1 | benzaldehyde, 2-hydroxy-4-methyl- | 2-hydroxy-4-methylbenzaldehyde | solid |
| 124 | 699-10-5 | disulfide, methyl phenylmethyl | methyl benzyl disulfide | 1.1382 |
| 125 | 7149-32-8 | 2-furancarboxylic acid, 2-phenylethyl ester | phenethyl 2-furoate | 1.1891 |
| 126 | 7217-59-6 | benzenethiol, 2-methoxy- | 2-methoxy-thiophenol | 1.1530 |
| 127 | 72927-84-5 | benzoic acid, 2-[[(4-hydroxy-3-methoxyphenyl)methylene]amino]-,methyl ester | benzoic acid, 2-[[(4-hydroxy-3-methoxyphenyl)methylene]amino]-,methyl ester | solid |
| 128 | 72987-59-8 | ethanol, 2-(4-methylphenoxy)-1-(2-phenylethoxy)- | algix synarome | 1.1309 |
| 129 | 7492-65-1 | benzeneacetic acid, 3-phenyl-2-propenyl ester | cinnamyl phenylacetate | solid |
| 130 | 7493-63-2 | benzoic acid, 2-amino-, 2-propenyl ester | allyl anthranilate | solid |
| 131 | 75147-23-8 | bicyclo[3.2.1]octan-8-one, 1,5-dimethyl-, oxime | 1,5-dimethyl-bicyclo[3.2.1]octan-8-one, oxime- | solid |
| 132 | 7774-74-5 | 2-thiophenethiol | 2-thienyl mercaptan | 1.2297 |
| 133 | 7774-96-1 | phenol, 2-methoxy-4-(1-propenyl)-,formate | isoeugenyl formate | solid |
| 134 | 7779-16-0 | benzoic acid, 2-amino-, cyclohexyl ester | cyclohexyl anthranilate | solid |
| 136 | 79915-74-5 | benzoic acid, 2-hydroxy-, 2-(1-methylethoxy)ethyl ester | 2-isopropoxyethyl salicylate | solid |
| 137 | 81-14-1 | ethanone, 1-[4-(1,1-dimethylethyl)-2,6-dimethyl-3,5-dinitrophenyl]- | musk ketone | solid |
| 139 | 830-09-1 | 2-propenoic acid, 3-(4-methoxyphenyl)- | 4-methoxycinnamic acid | solid |
| 140 | 83-66-9 | benzene, 1-(1,1-dimethylethyl)-2-methoxy-4-methyl-3,5-dinitro- | musk ambrette | solid |

TABLE 3-continued

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 141 | 84-66-2 | 1,2-benzenedicarboxylic acid, diethyl ester | diethyl phthalate | 1.1221 |
| 142 | 85213-22-5 | ethanone, 1-(3,4-dihydro-2h-pyrrol-5-yl)- | 2-acetyl-1-pyrroline | 1.2592 |
| 143 | 85-91-6 | benzoic acid, 2-(methylamino)-, methyl ester | dimethyl anthranilate | solid |
| 144 | 87-05-8 | 2h-1-benzopyran-2-one, 7-ethoxy-4-methyl- | 4-methyl-7-ethoxycoumarin | solid |
| 145 | 87-22-9 | benzoic acid, 2-hydroxy-, 2-phenylethyl ester | phenethyl salicylate | solid |
| 146 | 87-25-2 | benzoic acid, 2-amino-, ethyl ester | ethyl anthranilate | 1.1408 |
| 147 | 87-29-6 | 2-propen-1-ol, 3-phenyl-, 2-aminobenzoate | cinnamyl anthranilate | solid |
| 149 | 882-33-7 | disulfide, diphenyl | phenyl disulfide | solid |
| 153 | 91-60-1 | 2-naphthalenethiol | 2-naphthyl mercaptan | solid |
| 154 | 93-08-3 | ethanone, 1-(2-naphthalenyl)- | methyl beta-naphthyl ketone | solid |
| 155 | 93-29-8 | phenol, 2-methoxy-4-(1-propenyl)-, acetate | isoeugenyl acetate | solid |
| 156 | 93-44-7 | 2-naphthalenol, benzoate | 2-naphthyl benzoate | solid |
| 157 | 93-99-2 | benzoic acid, phenyl ester | phenyl benzoate | solid |
| 159 | 94-13-3 | benzoic acid, 4-hydroxy-, propyl ester | propylparaben | solid |
| 160 | 941-98-0 | ethanone, 1-(1-naphthalenyl)- | methyl 1-naphthyl ketone | solid |
| 161 | 94278-27-0 | propanoic acid, 3-[(2-furanylmethyl)thio]-, ethyl ester | ethyl 3-(furfurylthio)propionate | solid |
| 162 | 94-41-7 | 2-propen-1-one, 1,3-diphenyl- | chalcone | solid |
| 163 | 94-44-0 | 3-pyridinecarboxylic acid, phenylmethyl ester | benzyl nicotinate | solid |
| 164 | 94-47-3 | benzoic acid, 2-phenylethyl ester | phenethyl benzoate | solid |
| 165 | 94-62-2 | piperidine, 1-[5-(1,3-benzodioxol-5-yl)-1-oxo-2,4-pentadienyl]-,(e,e)- | piperine | solid |
| 166 | 95-16-9 | Benzothiazole | benzosulfonazole | 1.1500 | b) cLogP balancing agents: Without being bound by theory, cLogP balancing agents are materials able to increase the total cLogP of said benefit agent composition in order to facilitate the emulsification of said benefit agent composition. Suitable cLogP balancing agents are listed in table 4.

TABLE 4 cLogP balancing agents

| | CAS | Common name | IUPAC name | cLogP |
|---|---|---|---|---|
| 1 | 6753-98-6 | Amyl_cinnamic_aldehyde,_dilinallyl_acetal | 1,4,8-Cycloundecatriene, 2,6,6,9-tetramethyl-, (E,E,E)- | 6.87 |
| 2 | 84-74-2 | Linolenic_acid | 1,2-Benzenedicarboxylic acid, dibutyl ester | 6.56 |
| 3 | 128-37-0 | Butyl_myristate | Phenol, 2,6-bis(1,1-dimethylethyl)-4-methyl- | 6.51 |
| 4 | 68480-17-1 | Ethyl_heptadecanoate | 3-Pentanone, 1-(2,6,6-trimethyl-2-cyclohexen-1-yl)- | 6.51 |
| 5 | 103-29-7 | Hexyl_dodecanoate | Benzene, 1,1'-(1,2-ethanediyl)bis- | 6.50 |
| 6 | 67801-47-2 | Hexyl_tetradecanoate | Benzoic acid, 2-[(3,7-dimethyl-2,6-octadienylidene)amino]-, methyl | 6.50 |
| 7 | 128-37-0 | Butyl_hexadecanoate | Phenol, 2,6-bis(1,1-dimethylethyl)-4-methyl- | 6.50 |
| 8 | 629-94-7 | Decanoic_acid,_decyl_ester | Heneicosane | 6.50 |
| 9 | 112-41-4 | Isopropyl_palmitate | 1-Dodecene | 6.47 |
| 10 | 10402-47-8 | 2-Methylpropyl_tetradecanoate | Pentanoic acid, 3,7-dimethyl-2,6-octadienyl ester, (E)- | 6.46 |
| 11 | 128-37-0 | Ethyl_pentadecanoate | Phenol, 2,6-bis(1,1-dimethylethyl)-4-methyl- | 6.46 |
| 12 | 117-98-6 | 3-Methylbutyl_tetradecanoate | 6-Azulenol, 1,2,3,3a,4,5,6,8a-octahydro-4,8-dimethyl-2-(1-methylethylidene)-, acetate | 6.45 |
| 13 | 122-62-3 | Ethyl_stearate | Decanedioic acid, bis(2-ethylhexyl) ester | 6.45 |
| 14 | 20407-84-5 | Isopropyl_myristate | 2-Dodecenal, (E)- | 6.44 |

TABLE 4-continued cLogP balancing agents

| | | | | |
|---|---|---|---|---|
| 15 | 5132-75-2 | Hexadecyl_acetate | Heptanoic acid, octyl ester | 6.44 |
| 16 | 67801-47-2 | 2-Methylpropyl_hexadecanoate | Benzoic acid, 2-[(3,7-dimethyl-2,6-octadienylidene)amino]-, methyl | 6.43 |
| 17 | 112-40-3 | Methyl_hexadecanoate | Dodecane | 6.41 |
| 18 | 3915-83-1 | Ethyl_oleate | Butanoic acid, 3-methyl-, 3,7-dimethyl-2,6-octadienyl ester, (Z)- | 6.41 |
| 19 | 10024-64-3 | Methyl_stearate | Octanoic acid, 1-ethenyl-1,5-dimethyl-4-hexenyl ester | 6.41 |
| 20 | 6624-58-4 | Decyl_phthalate | Hexanoic acid, 1-methylhexyl ester | 6.40 |
| 21 | 112-37-8 | 9-Heptadecanone | Undecanoic acid | 6.40 |
| 22 | 1166-52-5 | Methyl_oleate | Benzoic acid, 3,4,5-trihydroxy-, dodecyl ester | 6.35 |
| 23 | 128-37-0 | alpha-Camphorene | Phenol, 2,6-bis(1,1-dimethylethyl)-4-methyl- | 6.34 |
| 24 | 128-37-0 | Butyl_oleate | Phenol, 2,6-bis(1,1-dimethylethyl)-4-methyl- | 6.31 |
| 25 | 65405-77-8 | Ethyl_linoleate | Benzoic acid, 2-hydroxy-, 3-hexenyl ester, (Z)- | 6.31 |
| 26 | 3915-83-1 | Ethyl_myristate | Butanoic acid, 3-methyl-, 3,7-dimethyl-2,6-octadienyl ester, (Z)- | 6.30 |
| 27 | 6624-58-4 | Dodecyl_isobutyrate | Hexanoic acid, 1-methylhexyl ester | 6.30 |
| 28 | 20407-84-5 | Butyl_stearate | 2-Dodecenal, (E)- | 6.29 |
| 29 | 128-37-0 | Didodecyl_phthalate | Phenol, 2,6-bis(1,1-dimethylethyl)-4-methyl- | 6.28 |
| 30 | 112-37-8 | Dodecyl_butyrate | Undecanoic acid | 6.27 |
| 31 | 1731-88-0 | Methyltetradecylketone | Tridecanoic acid, methyl ester | 6.27 |
| 32 | 68039-38-3 | Adimoll_DO | 2-Butenoic acid, 3,7-dimethyl-6-octenyl ester | 6.25 |
| 33 | 5132-75-2 | 2-Methylpropyl_dodecanoate | Heptanoic acid, octyl ester | 6.24 |
| 34 | 644-08-6 | 4-Methylphenyl_dodecanoate | 1,1'-Biphenyl, 4-methyl- | 6.19 |
| 35 | 2153-28-8 | alpha-bisabolene | Butanoic acid, 1-methyl-1-(4-methyl-3-cyclohexen-1-yl)ethyl ester | 6.19 |
| 36 | 110-38-3 | Ethylhexyl_palmitate | Decanoic acid, ethyl ester | 6.18 |
| 37 | 101-86-0 | Stearic_acid,_isopentyl_ester | Octanal, 2-(phenylmethylene)- | 6.17 |
| 38 | 111-01-3 | Squalene | Tetracosane, 2,6,10,15,19,23-hexamethyl- | 6.17 |
| 39 | 5132-75-2 | Benzyl_laurate | Heptanoic acid, octyl ester | 6.13 |
| 40 | 112-37-8 | 2-Pentadecanone | 2-Pentadecanone | 6.10 |
| 41 | 24717-85-9 | Methyl_linoleate | 2-Butenoic acid, 2-methyl-, 3,7-dimethyl-6-octenyl ester, (E)- | 6.09 |
| 42 | 68039-38-3 | iso_Propyl_dodecanoate | 2-Butenoic acid, 3,7-dimethyl-6-octenyl ester | 6.05 |
| 43 | 1166-52-5 | Methyl_myristate | Benzoic acid, 3,4,5-trihydroxy-, dodecyl ester | 6.02 |
| 44 | 112-63-0 | Palmitoleic_acid | 9,12-Octadecadienoic acid (Z,Z)-, methyl ester | 6.01 |
| 45 | 141-16-2 | Phytyl_acetate | Butanoic acid, 3,7-dimethyl-6-octenyl ester | 6.01 |
| 46 | 128-37-0 | Propyl_laurate | Phenol, 2,6-bis(1,1-dimethylethyl)-4-methyl- | 6.01 |
| 47 | 10402-47-8 | Linalyl_octanoate | Pentanoic acid, 3,7-dimethyl-2,6-octadienyl ester, (E)- | 6.00 |
| 48 | 79-78-7 | Nerolidyl_isobutyrate | 1,6-Heptadien-3-one, 1-(2,6,6-trimethyl-2-cyclohexen-1-yl)- | 5.98 |
| 49 | 68039-38-3 | 6,10,14-trimethyl-2-Pentadecanone | 2-Butenoic acid, 3,7-dimethyl-6-octenyl ester | 5.98 |
| 50 | 84012-64-6 | 2-Pentadecanone,_6,10,14-trimethyl- | 1-Cyclopentene-1-propanol, .beta.,.beta.,2-trimethyl-5-(1- | 5.98 |
| 51 | 112-54-9 | Ethyl_linolenate | Dodecanal | 5.97 |
| 52 | 24717-85-9 | 1-Dodecene | 2-Butenoic acid, 2-methyl-, 3,7-dimethyl-6-octenyl ester, (E)- | 5.95 |
| 53 | 3915-83-1 | alpha-Farnesene | Butanoic acid, 3-methyl-, 3,7-dimethyl-2,6-octadienyl ester, (Z)- | 5.95 |
| 54 | 6281-40-9 | n-Pentyl_decanoate | Hexanoic acid, 3-phenylpropyl ester | 5.95 |
| 55 | 128-37-0 | Heptyl_octanoate | Phenol, 2,6-bis(1,1-dimethylethyl)-4-methyl- | 5.94 |
| 56 | 68459-99-4 | Oleic_acid | 1-Penten-3-one, 4-methyl-1-(2,6,6-trimethyl-2-cyclohexen-1-yl)- | 5.94 |
| 57 | 137085-37-1 | Octyl_heptanoate | 1-Penten-3-ol, 1-(2,6,6-trimethyl-1-cyclohexen-1-yl)-, acetate | 5.94 |
| 58 | 7493-82-5 | Myristaldehyde | Heptanoic acid, pentyl ester | 5.86 |
| 59 | 67801-47-2 | Cyclohexyl_amyl_sulfide_in_diethyl_phthalate | Benzoic acid, 2-[(3,7-dimethyl-2,6-octadienylidene)amino]-, methyl | 5.77 |
| 60 | 67874-72-0 | Hendecane | Cyclohexanol, 2-(1,1-dimethylpropyl)-, acetate | 5.73 |
| 61 | 150-60-7 | (+)-Cuparene | Disulfide, bis(phenylmethyl) | 5.73 |
| 62 | 101-86-0 | Lauryl_acetate | Octanal, 2-(phenylmethylene)- | 5.73 |

TABLE 4-continued cLogP balancing agents

| | | | | |
|---|---|---|---|---|
| 63 | 3915-83-1 | Dodecane | Butanoic acid, 3-methyl-, 3,7-dimethyl-2,6-octadienyl ester, (Z)- | 5.72 |
| 64 | 3915-83-1 | Hexadecanenitrile (9CI) | Butanoic acid, 3-methyl-, 3,7-dimethyl-2,6-octadienyl ester, (Z)- | 5.72 |
| 65 | 106-29-6 | Benzoic acid, 3,4,5-trihydroxy-, dodecyl ester (9CI) | Butanoic acid, 3,7-dimethyl-2,6-octadienyl ester, (E)- | 5.68 |
| 66 | 67801-47-2 | 2-Methylpropyl decanoate | Benzoic acid, 2-[(3,7-dimethyl-2,6-octadienylidene)amino]-, methyl | 5.68 |
| 67 | 67801-47-2 | Butyl decanoate | Benzoic acid, 2-[(3,7-dimethyl-2,6-octadienylidene)amino]-, methyl | 5.67 |
| 68 | 638-25-5 | Methyl linolenate | Octanoic acid, pentyl ester | 5.64 |
| 69 | 3915-83-1 | beta-Guaiene | Butanoic acid, 3-methyl-, 3,7-dimethyl-2,6-octadienyl ester, (Z)- | 5.63 |
| 70 | 67801-47-2 | Dipentyl sulphide | Benzoic acid, 2-[(3,7-dimethyl-2,6-octadienylidene)amino]-, methyl | 5.62 |
| 71 | 51532-26-4 | Hexyl octanoate | Octanoic acid, 3,7-dimethyl-2,6-octadienyl ester, (E)- | 5.62 |
| 72 | 59056-62-1 | Farnesyl methyl ether | 2,3b-Methano-3bH-cyclopenta[1,3]cyclopropa[1,2]benzene-4-methanol, octahydro-7,7,8,8-tetramethyl-, acetate | 5.60 |
| 73 | 463-40-1 | 1,1,6-Trimethyltetraline | 9,12,15-Octadecatrienoic acid, (Z,Z,Z)- | 5.58 |
| 74 | 7774-82-5 | alpha-Santalene | 2-Tridecenal | 5.56 |
| 75 | 493-01-6 | Verdantiol | Naphthalene, decahydro-, cis- | 5.56 |
| 76 | 128-37-0 | Helvetolide | Phenol, 2,6-bis(1,1-dimethylethyl)-4-methyl- | 5.56 |
| 77 | 67801-47-2 | Dicyclohexyl disulfide | Benzoic acid, 2-[(3,7-dimethyl-2,6-octadienylidene)amino]-, methyl | 5.55 |
| 78 | 128-37-0 | (E,E)-6,10,14-trimethyl-5,9,13-Pentadecatrien-2-one | Phenol, 2,6-bis(1,1-dimethylethyl)-4-methyl- | 5.54 |
| 79 | 67801-47-2 | Citronellyl caproate | Benzoic acid, 2-[(3,7-dimethyl-2,6-octadienylidene)amino]-, methyl | 5.52 |
| 80 | 67801-47-2 | 2,6,10-Trimethylundecanal | Benzoic acid, 2-[(3,7-dimethyl-2,6-octadienylidene)amino]-, methyl | 5.49 |
| 81 | 128-37-0 | Cadinene | Phenol, 2,6-bis(1,1-dimethylethyl)-4-methyl- | 5.47 |
| 82 | 32214-91-8 | Celestolide | Bicyclo[7.2.0]undec-3-en-5-ol, 4,11,11-trimethyl-8-methylene-, acetate | 5.47 |
| 83 | 128-37-0 | Linalyl phenylacetate | Phenol, 2,6-bis(1,1-dimethylethyl)-4-methyl- | 5.46 |
| 84 | 638-25-5 | Tridecanal | Octanoic acid, pentyl ester | 5.44 |
| 85 | 67801-47-2 | 2-Octylthiophene | Benzoic acid, 2-[(3,7-dimethyl-2,6-octadienylidene)amino]-, methyl | 5.44 |
| 86 | 128-37-0 | 3-Tridecanone | Phenol, 2,6-bis(1,1-dimethylethyl)-4-methyl- | 5.44 |
| 87 | 67801-47-2 | Galaxolide | Benzoic acid, 2-[(3,7-dimethyl-2,6-octadienylidene)amino]-, methyl | 5.43 |
| 88 | 128-37-0 | 3-Methyldodecanenitrile | Phenol, 2,6-bis(1,1-dimethylethyl)-4-methyl- | 5.39 |
| 89 | 1731-86-8 | Undecanal diethyl acetal | Undecanoic acid, methyl ester | 5.38 |
| 90 | 6876-13-7 | 2,2,4,6,6-Pentamethylheptane | Bicyclo[3.1.1]heptane, 2,6,6-trimethyl-, (1.alpha.,2.beta.,5.alpha.)- | 5.35 |
| 91 | 79-78-7 | beta-Patchoulline | 1,6-Heptadien-3-one, 1-(2,6,6-trimethyl-2-cyclohexen-1-yl)- | 5.34 |
| 93 | 79-78-7 | Octyl phenylacetate | 1,6-Heptadien-3-one, 1-(2,6,6-trimethyl-2-cyclohexen-1-yl)- | 5.32 |
| 94 | 117-98-6 | Undecyl acetate | 6-Azulenol, 1,2,3,3a,4,5,6,8a-octahydro-4,8-dimethyl-2-(1-methylethylidene)-, acetate | 5.30 |
| 95 | 638-25-5 | Octyl 2-methylbutyrate | Octanoic acid, pentyl ester | 5.29 |
| 96 | 67801-47-2 | delta-Tetradecalactone | Benzoic acid, 2-[(3,7-dimethyl-2,6-octadienylidene)amino]-, methyl | 5.29 |
| 97 | 37165-63-2 | Octyl isovalerate | Nonanoic acid, 2-hexyl- | 5.29 |
| 98 | 68039-38-3 | Isobutyl nonanoate | 2-Butenoic acid, 3,7-dimethyl-6-octenyl ester | 5.28 |
| 100 | 39900-38-4 | Rhodinyl butyrate | 1H-3a,7-Methanoazulen-6-ol, octahydro-3,6,8,8-tetramethyl-, formate, [3R-(3.alpha.,3a.beta.,6.alpha.,7.beta.,8a.alpha.)]- | 5.26 |
| 101 | 23726-92-3 | Cyclohexanone, 2,4-bis(1,1-dimethylethyl)- | 2-Buten-1-one, 1-(2,6,6-trimethyl-1-cyclohexen-1-yl)-, (Z)- | 5.26 |
| 102 | 67801-47-2 | Dihexyl fumarate | Benzoic acid, 2-[(3,7-dimethyl-2,6-octadienylidene)amino]-, methyl | 5.26 |
| 103 | 128-37-0 | Isopropyl 10-undecenoate | Phenol, 2,6-bis(1,1-dimethylethyl)-4-methyl- | 5.25 |

TABLE 4-continued cLogP balancing agents

| CAS Number | Common name | IUPAC Name | Vapor Pressure Log of mm of Hg | Boiling point (° C.) |
|---|---|---|---|---|
| 40785-62-4 | 14-Oxabicyclo[10.3.0]-2-pentadecene | Cyclododeca[c]furan, 1,3,3a,4,5,6,7,8,9,10,11,13a-dodecahydro- | −12.50 | 149.3 |
| 67785-71-1 | Amyl cinnamic aldehyde, dilinallyl acetal | Benzene, [2-[his [(1-ethenyl-1,5-dimethyl-4-hexenyl)oxy]methyl]-1- | −12.19 | 374.8 |
| 67785-74-4 | Undecylenic aldehyde digeranyl acetal | 1-Undecene, 11,11-bis[(3,7-dimethyl-2,6-octadienyl)oxy]- | −10.92 | 158.4 |
| 111-02-4 | Squalene | 2,6,10,14,18,22-Tetracosahexaene, 2,6,10,15,19,23-hexamethyl-, (all-E)- | −10.51 | 247.0 |
| 111-01-3 | Squalane | Tetracosane, 2,6,10,15,19,23-hexamethyl- | −8.93 | 417.3 |
| 142-77-8 | Butyl oleate | 9-Octadecenoic acid (Z)-, butyl ester | −6.54 | 358.4 |
| 1191-41-9 | Ethyl linolenate | 9,12,15-Octadecatrienoic acid, ethyl ester, (Z,Z,Z)- | −6.37 | 294.5 |
| 544-35-4 | Ethyl linoleate | 9,12-Octadecadienoic acid (Z,Z)-, ethyl ester | −5.90 | 305.1 |
| 111-62-6 | Ethyl oleate | 9-Octadecenoic acid (Z)-, ethyl ester | −5.70 | 337.0 |
| 140-25-0 | Benzyl laurate | Dodecanoic acid, phenylmethyl ester | −5.35 | 296.3 |
| 122-69-0 | Cinnamyl cinnamate | 2-Propenoic acid, 3-phenyl-, 3-phenyl-2-propenyl ester | −5.23 | 351.2 |
| 10402-33-2 | Eugenyl phenylacetate | Benzeneacetic acid, 2-methoxy-4-(2-propenyl)phenyl ester | −5.22 | 372.9 |
| 102-22-7 | Geranyl phenylacetate | Benzeneacetic acid, 3,7-dimethyl-2,6-octadienyl ester, (E)- | −5.10 | 272.9 |
| 7143-69-3 | Linalyl phenylacetate | Benzeneacetic acid, 1-ethenyl-1,5-dimethyl-4-hexenyl ester | −5.04 | 329.3 |
| 139-70-8 | Citronellyl phenylacetate | Benzeneacetic acid, 3,7-dimethyl-6-octenyl ester | −4.83 | 283.3 |
| 142-91-6 | Isopropyl palmitate | Hexadecanoic acid, 1-methylethyl ester | −4.45 | 331.3 |
| 544-63-8 | Myristic acid | Tetradecanoic acid | −3.86 | 330.4 |
| 67634-02-0 | Phenylacetaldehyde digeranyl acetal | Benzene, [2,2-bis[(3,7-dimethyl-2,6-octadienyl)oxy]ethyl]- | −3.31 | 284.3 |
| 629-97-0 | n-Docosane | Docosane | −3.23 | 318.8 |
| 67785-69-7 | Amyl cinnamic aldehyde, digeranyl acetal | Benzene, [2-[bis[(3,7-dimethyl-2,6-octadienyl)oxy]methyl]-1- | −3.08 | 296.8 |
| 65416-19-5 | Phenylacetaldehyde dibenzyl acetal | Benzene, 1,1'-[(2-phenylethylidene)bis(oxymethylene)]bis- | −2.25 | 266.5 |
| 57-11-4 | Stearic acid | Octadecanoic acid | −1.73 | 246.2 |
| 7493-80-3 | alpha-Amylcinnamyl isovalerate | Butanoic acid, 3-methyl-, 2-(phenylmethylene)heptyl ester | −1.68 | 248.4 | c) Vapor pressure balancing agents: the vapor pressure provides a gauge of the rate of evaporation and the odor strength of the perfume composition. While not being bound by theory, when the vapor pressure of the encapsulate's core is balanced, the encapsulate provides a longer lasting and more consistent core material release.

We can use materials having a low vapor pressure to improve the longevity of the release (see table below), or we can even use materials with a high vapor pressure for a fast release (see Table 5).

TABLE 5 vapor pressure balancing agents

| CAS Number | Common name | IUPAC Name | Vapor Pressure Log of mm of Hg | Boiling point (° C.) |
|---|---|---|---|---|
| 6175-49-1 | Decyl methyl ketone | 2-Dodecanone | 0.67 | 160.8 |
| 112-44-7 | Undecanal | Undecanal | −1.49 | 236.8 |
| 7289-52-3 | Decyl methyl ether | Decane, 1-methoxy- | −1.19 | 217.5 |
| 112-40-3 | Dodecane | Dodecane | −0.75 | 195.2 |
| 22810-10-2 | Citronellyl ethyl ether | Octane, 1-ethoxy-3,7-dimethyl- | −1.03 | 207.8 |
| 112-41-4 | 1-Dodecene | 1-Dodecene | −1.00 | 196.7 |
| 1120-21-4 | Hendecane | Undecane | −0.25 | 177.5 |

TABLE 5-continued vapor pressure balancing agents

| CAS Number | Common name | IUPAC Name | Vapor Pressure Log of mm of Hg | Boiling point (° C.) |
|---|---|---|---|---|
| 124-18-5 | n-Decane | n-Decane | 0.24 | 159.6 |
| 2436-90-0 | Dihydromyrcene | 1,6-Octadiene, 3,7-dimethyl- | −0.22 | 156.7 |

Process of Making Polyamide, Polyester, Polycarbonate, Polyurea and Polyurethane Encapsulates A process of making a consumer product comprising combining a consumer product adjunct material and a population of encapsulates is disclosed.

In one aspect of said process, said population of encapsulates might be made by:
  a) preparing a core material comprising a benefit agent selected from the group consisting of a perfume composition, a silicone, a biocontrol agent, a flavor, a heating or cooling agent, a drug and combinations thereof.
  b) preparing a first solution comprising, based on total solution weight, from about 0.1% to about 5%, an emulsifier, preferably polyvinyl alcohol and cooling this first solution, preferably to a temperature of from about 0° C. to about 25° C.;
  c) preparing a second solution comprising, based on total solution weight, from about 65% to about 97% core material, and one or more hydrophobic monomers, comprising di- or triacyl chlorides, diisocyanates and/or bischloroformates. In one aspect such water immiscible organic monomer may comprise the azobenzene moiety;
  d) preparing a third solution comprising based on total weight from about 10% to about 90% water, and one or more hydrophilic monomers comprising di-amines, tri-amines, triols and/or diols. In one aspect such water miscible monomers may comprise the azobenzene moiety;
  e) forming a first composition at temperature of from about 0° C. to about 40° C., by either combining said second solution and said first solution and emulsifying said first composition;
  f) combining said first composition and said third solution to form a second composition and optionally combining any processing aids and said second composition;
  g) stirring said second composition for at least 15 minutes at a temperature of from about 0° C. to about 40° C. and optionally combining any processing aids to said second composition;
  h) optionally combining any scavenger material, neutralizing agent, structurant, salts and/or anti-agglomeration agent with said second composition during step g.) or thereafter;
  i) optionally spray drying or agglomerating said second composition;
  j) combining said second composition with one or more consumer product adjuncts.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.), ProcepT (Zelzate, Belgium), Vidrafoc (Barcelona, Spain).

Process of Making Acrylate Encapsulates

In one aspect, a process of making particles, each of said particles independently having a particle size of from about 2 microns to about 80 microns, from about 5 microns to about 50 microns or even from about 10 microns to about 30 microns, each particle comprising:
  a.) a core that comprises, based on total particle weight, from about 6% to about 99.9%, from about 11% to about 95%, or from about 50% to about 75%, of a benefit agent and from about 0.1% to about 94%, from about 5% to about 89%, or even from about 25% to about 50% of a partitioning modifier and/or density modifier; and
  b.) a shell that encapsulates said core, said shell comprising, based on total shell weight, from about 50% to about 100%, from about 70% to about 100% or even from about 80% to about 100% of a polyacrylate is disclosed.

In one aspect, a process of making a particle comprising:
  a.) reacting a multifunctional acrylate monomer and/or multifunctionalacrylate oligomer, in one aspect a multifunctional methacrylate monomer and/or multifunctional methacrylate oligomer, in a benefit agent comprising a partitioning modifier and/or density modifier with a composition comprising:
    i) an amine acrylate and/or methacrylate and a strong acid; or
    ii) a carboxylic acid acrylate and/or methacrylate monomer and a strong base; or
    iii) an amine acrylate and/or methacrylate monomer and a carboxylic acid acrylate and/or carboxylic acid methacrylate monomer
    iv) an azobenzene monomer
    to form a core composition,
  b.) forming an emulsion comprising said core composition, a surfactant, in one aspect anionic, cationic or neutral surfactant, and water;
  c.) curing said emulsion by applying a sufficient amount of thermal, UV, and/or electron beam energy to said emulsion to induce sufficient free-radical polymerization to form a particle having a core comprising said benefit agent and a shell comprising an acrylate, said shell encapsulating said benefit agent is disclosed.

Process of Making Urea and/or Melamine-Formaldehyde Encapsulates

In one aspect, a process comprising:
  a.) preparing a first solution comprising, based on total solution weight from about 20% to about 90%, from about 40% to about 80%, or even from about 60% to about 80% water, a first emulsifier and a first resin, the ratio of said first emulsifier and said first resin being from about 0.1:0 to about 10:0, from about 0.1:1 to about 10:1, from about 0.5:1 to about 3:1, or even from about 0.8:1 to about 1.1:1;

b.) preparing a second solution comprising based on total solution weight from about 20% to about 95% water, a second emulsifier, a second resin, and an azo containing resin the ratio of said second emulsifier and said second resin being from about 0:1 to about 3:1, from about 0.04:1 to about 0.2:1, or even from about 0.05:1 to about 0.15:1;

c.) combining a core material and said first solution to form a first composition;

d.) emulsifying said first composition;

e.) combining said first composition and said second solution to form a second composition and optionally combining any processing aids and said second composition—said first composition and said second solution may be combined in any order but in one aspect said second solution is added to said first composition or said second solution and said first composition are combined simultaneously;

f.) mixing said second composition for at least 15 minutes, at least 1 hour or even from about 4 hours to about 100 hours at a temperature of from about 25° C. to about 100° C., from about 45° C. to about 90° C., or even from about 50° C. to about 80° C. heat and optionally combining any processing aids to said second composition;

g.) optionally combining any scavenger material, structurant, and/or anti-agglomeration agent with said second composition during step f.) or thereafter—such materials may be combined in any order but in one aspect the scavenger material is combined first, any structurant second, and then anti-agglomeration agent is combined; and h.) optionally spray drying said second composition is disclosed.

Adjunct Materials

While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, UV absorbers, additional perfume and perfume delivery systems, structure elasticizing agents, thickeners/structurants, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential for each consumer product embodiment of the present invention. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, thickeners/structurants, fabric softeners, carriers, hydrotropes, processing aids and/or pigments. However, when one or more adjuncts is present, such one or more adjuncts may be present as detailed below.

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Suitable thickeners/structurants and useful levels of same are described in U.S. Patent Application Publication No. 2005/0130864 A1 and U.S. Pat. Nos. 7,169,741 B2 and 7,297,674 B2. In one aspect, the thickener may be a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 sec$^{-1}$ shear rate and at 21° C., of from 1 to 7,000 cps and a viscosity at low shear (0.5 sec$^{-1}$ shear rate at 21° C.) of greater than 1000 cps, or even 1,000 cps to 200,000 cps. In one aspect, for cleaning and treatment compositions, such rheology modifiers impart to the aqueous liquid composition a high shear viscosity, at 20 sec$^{-1}$ and at 21° C., of from 50 to 3,000 cps and a viscosity at low shear (0.5 sec$^{-1}$ shear rate at 21° C.) of greater than 1,000 cps, or even 1,000 cps to 200,000 cps. Viscosity according to the present invention is measured using an AR 2000 rheometer from TA instruments using a plate steel spindle having a plate diameter of 40 mm and a gap size of 500 µm. The high shear viscosity at 20 sec$^{1}$ and low shear viscosity at 0.5 sec$^{-1}$ can be obtained from a logarithmic shear rate sweep from 0.1 sec$^{-1}$ to 25 sec$^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are selected from the group consisting of polyacrylates, polymeric gums, other non-gum polysaccharides, and combinations of these polymeric materials.

Generally, the rheology modifier will comprise from about 0.01% to about 1% by weight, from about 0.05% to about 0.75% by weight, or even from about 0.1% to about 0.5% by weight, of the compositions herein.

Structuring agents which are especially useful in the compositions of the present invention comprises non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers may include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may compriser dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc under the tradename Carbopol Aqua 30®. In the absence of rheology modifier and in order to impart the desired shear thinning characteristics to the liquid composition, the liquid composition can be internally structured through surfactant phase chemistry or gel phases.

UV Absorbers—in certain consumer product embodiments of the present invention, the photo-responsive encapsulates of the present invention may be stabilized against premature release by exposure to light of a sufficient wavelength during storage by incorporation of a suitable UV-absorbing ingredients into the composition. Any suitable UV-absorbing composition may be employed, but particularly preferred are those which do not impart an unpleasant color or odor to the composition, and which do not adversely affect the rheology of the product. Non-limiting examples of UV-absorbing ingredients include avobenzone, cinoxate, ecamsule, menthyl anthranilate, octyl methoxycinnamate, octyl salicylate, oxybenzone, sulisobenzone, and combinations thereof. Other suitable UV-absorbing ingredients are disclosed in U.S. Pat. No. 6,159,918, which is incorporated herein by reference. Applicants have surprisingly found that the use of such UV-absorbing ingredients do not compromise the light-activated performance of encapsulates of the present invention. Without wishing to be bound by theory, it is believed that in many consumer product applications, e.g., cleaning compositions including laundry detergents, shampoos and body washes, the UV absorbing ingredient is washed down the drain while the encapsulates of the present invention are retained in an efficacious amount on the surface of interest where they are available to release their contents on subsequent exposure to light of a sufficient wavelength. In other cleaning compositions or leave-on consumer products, e.g., floor cleaning compositions, drapery and upholstery refreshers, body lotions, and hair styling products, it is believed that the UV-absorbing ingredients dry down to a thin film after application, allowing the encapsulates of the present invention to sit atop or extend above the film. This allows and efficacious amount of light of the desired wavelength to reach the encapsulates and effect the release of the benefit agents.

Packaging Materials

The embodiments of the present invention may be protected against premature release caused by exposure to light of a sufficient wavelength during storage by judicious selection of packaging. Any suitable package or package material that reduces or eliminates penetration of light into the composition contained therein may be employed. Non-limiting examples of packaging materials include coated cardboard, fiberboard or paperboard, colored polyolefins including HDPE, LDPE, LLDPE, and combinations thereof, polypropylene, and coated metal foils, among others.

In some cases, the formulator may wish to employ a more transparent or translucent, colorless packaging material to display the contents contained therein. Non-limiting examples of such transparent or translucent packaging materials include PET, PLA, PVC, HDPE, and blends or multi-layer combinations of these, among others. In these circumstances, it is understood that an effective means to prevent some wavelengths of light from penetrating through the packaging material, while allowing other wavelengths to pass through, is desirable so that the contents may be seen while still maintaining stability of the embodiments of present invention. Any suitable means to filter or absorb light of the desired wavelength may be employed. A particularly preferred means is to incorporate a UV-absorbing composition into the resin during manufacture of the package, a non-limiting example of which is described in GB 2 228 940, which is incorporated herein by reference. Other means are use of a label or sleeve which absorbs the required wavelength of light, non-limiting examples of which are described in EP 01280713 B1.

Processes of Making and Using Compositions

The embodiments of the compositions of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303 all of which are incorporated herein by reference.

Method of Use

Compositions disclosed herein that contain the encapsulate disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with an encapsulate as described herein or composition comprising said encapsulate and then optionally washed and/or rinsed. For purposes of this disclosure, washing includes but is not limited to, scrubbing, and mechanical agitation. The situs may comprise most any material, for example a fabric, fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

TEST METHODS

It is understood that the test methods that are disclosed in the Test Methods Section of the present application are used to determine the respective values of the parameters of Applicants' invention as such invention is described and claimed herein.

(1) Sample Preparation for Test Methods (if Sample is in a Slurry Form)

Before the encapsulate slurries can be used for the described tests, the sample is homogenized by shaking the sample for 20 minutes on a shaking table such as the Heidolph Promax 2020. Once homogenized, a 200 ml glass jar is filled with the slurry. This glass jar is then put on storage for the required time and condition. After the storage period, each 200 ml sample is again homogenized for 20 minutes on the shaking table. After homogenization the slurry is used for the experiments.

(1) Fracture Strength
a.) Place 1 gram of particles in 1 liter of distilled deionized (DI) water.
b.) Permit the particles to remain in the DI water for 10 minutes and then recover the particles by filtration, using a 60 mL syringe filter, 1.2 micron nitrocellulose filter (Millipore, 25 mm diameter).
c.) Determine the rupture force of 30 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.
d.) Use the 30 independent measurements from c.) above, and calculate the percentage of particles having a fracture strength within the claimed range fracture strength range.

(2) Mean Particle Size

The mean particle size of the wax coated particles is determined using a Lasentec M500L-316-K supplied by Mettler-Toledo, Inc., 1900 Polaris Parkway, Columbus, Ohio, 43240, US. The equipment is setup (Lasentec, FBRM Control Interface, version 6.0) as described in the Lasentec manuel, issued February 2000. Software setup and sample analysis is performed using Windows software (Windows XP, version 2002) in the WINDOWS manual.

(3) Particle Wall Thickness

All references to Leica Microsystems refer to the Company with Corporate Headquarters located at:
Leica Microsystems GmbH
Ernst-Leitz-Strasse 17-37
35578 Wetzlar All references to Drummond refer to the Company located at:
Drummond Scientific Company
500 Parkway, Box 700
Broomall, Pa. 19008

All references to Hitachi refer to the Company with Corporate Headquarters located at:
Hitachi High Technologies
24-14, Nishi-Shimbashi 1-chome, Minato-ku,
Tokyo 105-8717, Japan All references to Gatan refer to the Company with Corporate Headquarters located at:
Gatan, Inc.
5933 Coronado Lane
Pleasanton, Calif. 94588

All references to Quartz refer to the Company with offices located at:
Quartz Imaging Corporation
Technology Enterprise Facility III
6190 Agronomy Rd, Suite 406
Vancouver, B.C. Canada V6T 1Z3

Materials:
Methylcyclohexane—Alfa Aesar Catalogue Number A16057 or equivalent
Capillary Pipettes—Drummond Catalogue Number 5-000-1005 or equivalent
Flat Specimen Carrier—Leica Microsystems P/N 706897 or equivalent
Copper Washers—Leica Microsystems P/N 706867 or equivalent
Flat Specimen Pod—Leica Microsystems P/N 706839 or equivalent
Loading Device for Flat Specimen Holder—Leica Microsystems P/N 706832 or equivalent
Torque Wrench—Leica Microsystems P/N 870071 or equivalent
Allen Bit, 2 mm—Leica Microsystems P/N 870072 or equivalent
Forceps—Leica Microsystems P/N 840105 or equivalent
Gatan Planchette Collet—Gatan P/N PEP5099
Gatan Planchette Specimen Holder—Gatan P/N PEP1395

Instruments:
Scanning Electron Microscope—Hitachi Model S-5200 SEM/STEM or equivalent
High Pressure Freezer—Leica Microsystems Model 706802 EM Pact or equivalent
Cryotransfer Device—Gatan Model CT3500 or equivalent
Cryotransfer System—Gatan Model CT2500 or equivalent
Gatan ITC Temperature Controller—Gatan Model ITC502 or equivalent
Image Analysis Software—Quartz PCI Version 5 or equivalent Sample: Obtain the sample of microcapsules as per the procedure of 1 above entitled "Fracture Strength". 50 samples are required.

Test Procedure
1) Turn on the Leica Microsystems High Pressure Freezer (Leica Microsystems Model Number 706802).
2) Fill up the methylcyclohexane container on the High Pressure Freezer with methylcyclohexane (Alfa Aesar Cat. #A16057 or equivalent).
3) Fill up the liquid nitrogen dewar on the High Pressure Freezer.
4) Fill the liquid nitrogen bath on the High Pressure Freezer
5) The display on the High Pressure Freezer will show Load Sample on the front panel when the instrument is ready to use.
6) Start the Hitachi Model S-5200 SEM/STEM and set the Accelerating Voltage to 3.0 KV and the Emission Current to 20 µA.
7) Fill the Anti-contaminator Dewar located on the lower right side of the Hitachi Model S-5200 SEM/STEM microscope column with liquid nitrogen.
8) Fill the liquid nitrogen dewar on the Gatan Alto 2500 Cryotransfer System (Gatan Model CT2500). Replenish the liquid nitrogen until the dewar remains full. The device is ready to use when the prepchamber temperature reads below −190° C.
9) Place a copper washer (Leica Microsystems P/N 706867) on top of the flat specimen carrier such that the hole in the washer aligns with the well in the flat specimen carrier.
10) Take a glass capillary pipette (Drummond P/N 5-000-1005 or similar) and insert the provided wire plunger into one end of the pipette
11) Insert the pipette into the microcapsule dispersion and withdraw the plunger part way to pull a few microliters of the dispersion into the pipette.

12) Place the tip of the pipette in the well in the flat specimen carrier and push the plunger into the pipette to dispense a small amount of liquid until the well is just slightly overfilled.
13) Insert a 2 mm Allen key bit (Leica Microsystems P/N 870072) into the torque wrench (Leica Microsystems P/N 870071).
14) Using the torque wrench with the bit, loosen the Diamond Locking Screw in the Flat Specimen Pod (Leica Microsystems P/N 706839).
15) Place the Flat Specimen Holder and Copper Washer into the Flat Specimen Pod.
16) Use the torque wrench with the 2 mm Allen key bit to tighten the Diamond Locking Screw in the Flat Specimen Pod onto the specimen until the torque wrench clicks twice.
17) Attach the Loading Device for the Flat Specimen Holder (Leica Microsystems P/N 706832) to the Flat Specimen Pod by screwing it onto the exposed threads of the Diamond Locking Screw.
18) Place the Loading Device for the Flat Specimen Holder with the Flat Specimen Pod onto the EM Pact High Pressure Freezer (Leica Microsystems P/N 706802) and insert it into the High Pressure Freezer.
19) Freeze the specimen using the High Pressure Freezer.
20) Transfer the Flat Specimen Pod to the Unloading Station and unscrew the Loading Device for the Flat Specimen Carrier being careful to keep it immersed in the liquid nitrogen bath.
21) Using the torque wrench, loosen the Diamond Locking Screw.
22) Using tweezers with the tips cooled in liquid nitrogen until the liquid nitrogen stops boiling, remove the Flat Specimen Carrier from the Flat Specimen Pod and place it into a small container in the liquid nitrogen bath.
23) Place the Gatan CT3500 Cryotransfer Device (Gatan Model Number CT3500) into the Gatan Specimen Workstation.
24) Fill the liquid nitrogen dewar on the Gatan CT3500 Cryotransfer device and fill the dewar on the Gatan Specimen Workstation replenishing the liquid nitrogen as necessary until rapid boiling of the liquid nitrogen stops.
25) Transfer the Flat Specimen Holder to the Gatan Specimen Workstation while keeping it in a container of liquid nitrogen.
26) Using tweezers cooled in liquid nitrogen until the liquid nitrogen stops boiling, place the flat specimen holder into the Gatan Planchette Collet (Gatan P/N PEP5099) and press down firmly.
27) Place the assembly from step 26 into the Gatan Planchette Specimen Holder (Gatan P/N PEP1395) and press down firmly.
28) Push the Gatan Cryotransfer device back into the Gatan Specimen Workstation.
29) Using the Gatan supplied 5 mm Friction Tool, screw the Gatan Planchette Specimen Holder into the Gatan Cryotransfer device.
30) Remove the Gatan Cryotransfer device from the Gatan Specimen Workstation and insert it into the Gatan Alto 2500 Cryotransfer System.
31) Attach the Gatan ITC Temperature Controller (Gatan Model Number ITC502) to the Gatan Cryotransfer device by attaching the Temperature Measurement Lead from the Gatan ITC controller to the connector on top of the Gatan Cryotransfer device.
32) Using the Gatan ITC Controller, raise the temperature of the specimen to −120° C.
33) Using the fracturing knife, break off the copper washer to fracture the specimen.
34) Reduce the temperature of the specimen below −160° C.
35) With the voltage set to 6 KV and the gas flow set to provide 10 mA sputter current, press the sputter button and once the current displays 10 mA, let the coater run for 60-90 seconds coating the specimen with gold/palladium.
36) Close the frost shield on the Gatan CT3500 Cryotransfer Device and transfer the specimen to the Hitachi S-5200 SEM/STEM.
37) Wait for the temperature of the Gatan CT3500 Cryotransfer device to stabilize, typically between −170° C. and −172° C.
38) Open the frost shield on the Gatan CT3500 Cryotransfer device by turning the frost shield control knob counter-clockwise.
39) Move the sample around using the stage control trackball, locate a broken microcapsule and adjust the magnification to 50,000 to 150,000×.
40) Adjust the focus and stigmation controls to obtain the best image.
41) Acquire an image of the cross-section of the capsule wall.

Calculations

1) Select the ruler tool in the Quartz PCI software.
2) Move the cursor to one edge of the microcapsule wall.
3) Click and hold the left mouse button while dragging the mouse cursor to the opposite side of the capsule wall keeping the drawn line perpendicular to the face of the capsule wall to measure the wall thickness.
4) Use 50 independent measurements (1 measurement for each capsule) to calculate the percentage of particles having a wall thickness in the claimed range.

(4) Perfume Leakage Index is Evaluated via % Liquid-liquid Extraction and Gas Chromatographic-mass Spectrometric Analysis When determining the perfume leakage index from Perfume Microcapsules in liquid detergent, a fresh sample of liquid detergent with equal level of free perfume (without Perfume Microcapsules) must also be analyzed in parallel for reference.

a) Preparation of an Internal Standard Solution:
  i. Stock solution of tonalid: Weigh 70 mg tonalid and add 20 ml hexane p.a.
  ii. Internal Standard Solution: Dilute 200 µl of stock solution in 20 ml hexane p.a.
  iii. Mix to homogenize b) Perfume Extraction from Liquid Detergent without Perfume Microcapsules (Reference)
  i. Weigh 2 g of liquid detergent product into an extraction vessel
  ii. Add 2 ml of Internal Standard Solution and close vessel
  iii. Extract perfume by gently turning the extraction vessel upside-down for 20 times (manually)
  iv. Add spoon tip of Sodium Sulphate
  v. After separation of layers, immediately transfer hexane-layer into Gas Chromatograph auto sampler-vial and cap vial
  vi. Inject splitless (1.5 µl) into Gas Chromatograph injection-port
  vii. Run Gas Chromatographic-Mass Spectrometric analysis c) Perfume Extraction from Liquid Detergent with Perfume Microcapsules
  i. Weigh 2 g of liquid detergent product into an extraction vessel
  ii. Add 2 ml of Internal Standard Solution and close vessel iii. Extract perfume by gently turning the extraction vessel upside-down for 20 times (manually)
iv. Add spoon tip of Sodium Sulphate
v. After separation of layers, immediately transfer hexane-layer into Gas Chromatograph auto sampler-vial and cap vial
vi. Inject splitless (1.5 µl) into Gas Chromatograph injection-port
vii. Run Gas Chromatographic-Mass Spectrometric analysis d) Calculation
i. The perfume leakage from capsules per individual Perfume Raw Material:

$$PerfumeLeakageIndex = \frac{\text{Area Perfume Raw Material caps} \cdot \text{Area Internal Standard Solution } ref \cdot \text{Weight } ref}{\text{Area Internal Standard Solution caps} \cdot \text{Area Perfume Raw Material } ref \cdot \text{Weight caps}}$$

(5) Determination of Free Perfume Composition in the Slurry via % Liquid-liquid Extraction and Gas Chromatographic-mass Spectrometric Analysis When determining the amount of free perfume composition in the microcapsule's slurry, a fresh sample in deionized water with equal level of free perfume composition (without Perfume Microcapsules) must also be analyzed in parallel for reference.

a) Preparation of Standard Solutions
i. Internal Standard Solution: Weigh 200 mg tonalid and add 25 ml hexane p.a. Mix to homogenize.
ii. Standard Solution: Dilute 2 grams of the perfume composition in 25 ml hexane p.a. Mix to homogenize.
b) Perfume Extraction from Deionized Water Containing Free Perfume Composition without Perfume Microcapsules (Reference)
i. Weigh 2 grams of deionized water into an extraction vessel
ii. Add 200 µL of Internal Standard Solution, 200 µL of Standard Solution and 10 mL of hexane and close vessel
iii. Extract perfume by gently turning the extraction vessel upside-down for 20 times (manually)
iv. Add spoon tip of Sodium Sulphate
v. After separation of layers, immediately transfer hexane-layer into Gas Chromatograph auto sampler-vial and cap vial
vi. Inject splitless (2 µl) into Gas Chromatograph injection-port
vii. Run Gas Chromatographic-Mass Spectrometric analysis
viii. Calculation of relative response factor $$RRF = \frac{m_P \cdot A_{IS}}{A_P \cdot m_{IS}}$$

wherein $m_P$ is the amount of perfume, $m_{IS}$ is the amount in grams of tonalid, $A_{IS}$ is the area of the tonalid and $A_P$ is the area of the perfume (sum of peaks)

c) Perfume Extraction from Perfume Encapsualte's Slurry
i. Weigh 0.5 grams of perfume encapsulate's slurry composition into an extraction vessel and add 0.5 grams demi-water and homogenize by swirling gently
ii. Add 100 L of Internal Standard Solution and 5 mL of hexane and close the vessel
iii. Extract perfume by gently turning the extraction vessel upside-down for 20 times (manually)
iv. Add spoon tip of Sodium Sulphate
v. After separation of layers, immediately transfer hexane-layer into Gas Chromatograph auto sampler-vial and cap vial
vi. Inject splitless (2.0 µL) into Gas Chromatograph injection-port
vii. Run Gas Chromatographic-Mass Spectrometric analysis
viii. Calculation The amount of perfume in the composition is calculated as follows:

$$\% \text{ Perfume} = \frac{A_{PE} \cdot RRF \cdot m_{ISE} \cdot 100}{A_{ISE} \cdot m_E}$$

wherein $m_{ISE}$ is the amount of tonalid in grams, $m_E$ is the amount of encapsulate's composition (slurry) in grams, RRF is the relative response facter calculated above, $A_{PE}$ is the area of perfume (sum of peaks) and $A_{ISE}$ the area of tonalid.

(6) Headspace Evaluation of Capsules in Hard Surface Applications

1) Clean 2.5×1.2×0.1 cm sample of hard surface material of interest (ceramic or porcelain tile, glass, wood, vinyl, etc) with soap and water, rinse thoroughly with water, ethanol and/or acetone. Dry at room temperature or 1 hour before transferring to oven (105 C) 24 hours.
2) Prepare hard surface cleaning product of interest, a test product containing the light triggered capsules and a reference product containing equivalent free perfume oil.
3) Dilute product according to application and carefully transfer 25 uL of test and reference solutions to individual 2.5×1.2×0.1 cm samples of hard surface material of interest. Apply the solutions diagonally across the slide then fill in the untreated spaces with remaining solution to coat entire surface area. Prepare enough test and reference and replicates of each for desired sampling times (see 4 below).
4) Allow the hard surface test and reference materials to dry in constant temperature and humidity room (75° C./50% R.H.) while exposing to electromagnetic radiation for desired time points, for example 15, 30, 60, 120, 240, and 360 minutes under a fluorescent or ultraviolet source.
5) Collect test and reference replicates at desired time points and seal individual hard surface samples into labeled 20 mL glass headspace vial. After equilibration, use comparative GCMS/SPME method to evaluate and compare perfume release profile of reference perfume oil to light triggered capsule. Calculate HRR (headspace response ratio) for specific time points, HRR=Headspace Area Count Capsule/Headspace Area Count Perfume Oil Reference GCMS/SPME Method:
Agilent 6890 GC equipped with 5974N mass spectrometer and Gerstel MPS2 automated SPME sampler, Supelco fiber 57298-U (1 cm DVB/CAR/PDMS)
Vial equilibration: 5 minutes, 30° C., no agitation; Fiber Exposure: 5 minutes, 30° C., no agitation; Desorption 3 minutes, 275° C.
GC Conditions 30m DB-1 or DB-5 column, initial temperature 50° C., 2 minutes, 10° C./minute, to 275° C. hold for 5 minutes (7) Olfactive Evaluation—Paired Comparison in Hard Surface Applications:
1) Clean (2) 30 cm×30 cm sample of hard surface material of interest (ceramic or porcelain tile, glass, wood, vinyl, etc) with soap and water, rinse thoroughly with water, ethanol and/or acetone. Dry at room temperature for 1 hour before transferring to oven (105° C.) 24 hours.
2) Clean (2) Olfactive Box Chambers (1.3×0.6×0.6 meter Lexan with preparation (0.3 m×0.6 m) and sampling doors (0.1 m×0.3 m) with clean paper towel and isopropyl alcohol.
3) Place a fan at the large opening; allowing the fan to flow into the chamber while the chamber fans are running for one hour.
4) Cover the bottom of the chamber with aluminum foil
5) Prepare hard surface cleaning product of interest, a test product containing the light triggered capsules and a reference product containing equivalent free perfume oil.
6) Apply five grams of the desired dilution of test and reference products to the 30 cm×30 cm hard surface material and disperse the solution evenly across tile with applicator (7×7 cm tared piece of Swiffer Sweeper Dry Refill attached to bottom of 8×8 cm weigh boat via Velcro). Record weight of damp Swiffer fabric to determine actual solution delivered to hard surface. Allow the hard surfaces to dry for fifteen minutes.
7) Place surfaces in center of chamber floor, Close chambers for fifteen minutes.
8) At least 20 trained panelists evaluate the intensity of the olfactive boxes via Paired Comparison Testing. Sensory Evaluation Techniques, 4th Ed.; Meilgard, et. al.; CRC Press 2007.
9) Hard Surfaces are removed from olfactive boxes until next predetermined time point of interest, at which time surfaces are returned to boxes for paired comparison assessment. Remove surfaces and repeat 4-9 for subsequent time points of interest.
10) Results are provided as % of panelists' preference.
(8) Headspace and Olfactive Evaluation of Capsules in Fabric Refresher Applications
1) Prepare Fabric Refresher product of interest, a test product containing the light triggered capsules and a reference product containing equivalent free perfume oil and transfer to Febreze spray bottles.
2) Attach Terry cloth to a vertical back board covered with aluminum foil. At a distance of 45 cm, apply 2 full sprays to each side of a tared 15×15 cm piece terry cloth. Weigh cloth and record exact weight of solution applied to fabric. Wrap each fabric in aluminum foil. Transfer and unwrap cloths in controlled environment with appropriate lighting. Expose the fabrics to the ideal light conditions and collect fabrics at desired time points.
3) Use Paired Comparison testing for Olfactive assessment, request 20 trained panelist to compare test to reference at desired time points. Sensory Evaluation Techniques, 4th Ed.; Meilgard, et. al.; CRC Press 2007.
4) For headspace, cut three 2.5×2.5 cm pieces cloth from three different replicates of reference and test treatments and seal in clean 20-mL headspace vial. After equilibration, use comparative GCMS/SPME method to evaluate and compare perfume release profile of reference perfume oil to light triggered capsule. Calculate HRR (headspace response ratio) for specific time points, HRR=Headspace Area Count Capsule/Headspace Area Count Perfume Oil Reference GCMS/SPME Method:
Agilent 6890 GC equipped with 5974N mass spectrometer and Gerstel MPS2 automated SPME sampler, Supelco fiber 57298-U (1 cm DVB/CAR/PDMS)
Vial equilibration: 5 minutes, 30° C., no agitation; Fiber Exposure: 5 minutes, 30° C., no agitation; Desorption 3 minutes, 275° C.; GC Conditions 30m DB-1 or DB-5 column, initial temperature 50° C., 2 minutes, 10° C./minute, to 275° C. hold for 5 minutes.

(9) Measurement of Released Perfume in the Slurry (Also Known as Encapsulate Suspension) After Exposure to Light After encapsulates' preparation the encapsulates' suspensions are kept in dark plastic bottles (Bottle LDPE 250 ml, brown wide neck+cap) provided by VWR international. Before UV irradiations the % of free perfume in the encapsulates' suspension is measured according to test method (5) Determination of free perfume composition in the slurry via % liquid-liquid extraction and gas chromatographic-mass spectrometric analysis.

Release test: 25 grams of encapsulates' suspension is stirred with a magnetic stirrer at 500 rpm and 22° C. for 30 minutes in a 30 mL white transparent bottle provided by Vidrafoc well closed. Then, the bottle is irradiated with UV light at 365 nm by treatment with a Vilber Lourmat VL-4. LC-230 V UV-lamp for 3 hours at 300 rpm. The lamp is set-up parallel to the bottle wall in a distance from about 20 cm. After 3 hours of irradiation, the lamp is switched off and the encapsulates' suspension is stirred for 10 minutes. 0.5 grams of the sample are collected for GC analysis as described in test method (5) Determination of free perfume composition in the slurry via % liquid-liquid extraction and gas chromatographic-mass spectrometric analysis. The rest of the encapsulates' suspension (aprox. 24.5 grams) is kept in the well closed in the original bottle, additionally protected with parafilm, for 24 h in the dark at 25° C. without stirring. After this time, the encapsulates' suspension is mixed for 30 minutes using a magnetic stirrer at 300 rpm in dark place and 0.5 grams of the slurry are analyzed following test method (5) Determination of free perfume composition in the slurry via % liquid-liquid extraction and gas chromatographic-mass spectrometric analysis. Once more, the bottle containing 24 grams of encapsulates' suspension is irradiated with UV light at 365 nm as described above and another sample of 0.5 grams is taken for analysis using method (5) Determination of free perfume composition in the slurry via % liquid-liquid extraction and gas chromatographic-mass spectrometric analysis.

EXAMPLES

Perfume Compositions Suitable to be Used:

TABLE 6

| | Perfume compositions | | | | | | | | | | | | |
|---|---|---|---|---|---|---|---|---|---|---|---|---|---|
| PRM No. | A | B | C | D | E | F | G | H | I | J | K | L | M |
| 1 | | | | | | | | | | | | | |
| 2 | 3.5 | | | | | | | | | | | | |
| 3 | 3.5 | | | | | | | | | | | 2.3 | 4 |
| 4 | | | | | | 3.6 | | | | | | | 10 |
| 5 | | | | | | | | | | | | | |
| 6 | | | | | | | | | | | | | |

TABLE 6-continued

| | Perfume compositions | | | | | | | | | | | | |
|---|---|---|---|---|---|---|---|---|---|---|---|---|
| PRM No. | A | B | C | D | E | F | G | H | I | J | K | L | M |
| 7 | | | | | | | | | | | | | |
| 8 | | | | | | | | | | | | | |
| 9 | | | | | | | | | | | | | |
| 10 | | | | | | | | | | | | | |
| 11 | 12.5 | 3.5 | | | | | | 1.5 | | | 3.6 | | |
| 12 | | | | | | | | | | | | | |
| 13 | | | 2 | | | | | | | | | | |
| 14 | | | | | | | | | | | | | |
| 15 | | | | | | | | | | | | | |
| 16 | | | | | | | | 3.5 | | | | | |
| 17 | | | | 2 | | | 2 | | | | | | |
| 18 | | | | 1.8 | | | | | | 2 | | | |
| 19 | | | | | | | | | | | | | |
| 20 | | | | | | | | | | | | | |
| 21 | | | | | | | | | | | | | |
| 22 | | | | | | | | | | | | 1.8 | |
| 23 | | | | | | | | | | | | | |
| 24 | | | | 3.2 | | | 3.8 | | | | | | |
| 25 | | | | | | | | | | | | | |
| 26 | | | | | | | 13 | | | | | | |
| 27 | | | | | | | | | | | | | |
| 28 | | | 12 | | | | | | | | | | |
| 29 | | | | | | | | | | | | | |
| 30 | | | | | | | | | | | | | |
| 31 | | | 13 | | | | | | | | | | |
| 32 | | | 1.8 | | 3.2 | 3.5 | | | | 2.3 | | | |
| 33 | | | 8.6 | | | 12.5 | | | | | | | |
| 34 | | | | | | | | | | | 8.6 | | |
| 35 | | | | | 4.3 | | | | | | | | |
| 36 | | | | 9 | | | | | | | | | |
| 37 | | | 3.5 | | | | 4 | | | | | | |
| 38 | | | 1.5 | | | | | | | | | | |
| 39 | | | | | | | | | | 13 | | | |
| 40 | | | | | | | | | | | 12.8 | | |
| 41 | | | | | | | | | | | | | |
| 42 | | | | 2 | | | | | | | | | |
| 43 | | | | | 1.8 | | | | | 3.8 | | | 1 |
| 44 | | | 3 | | | | | 3.6 | 2.3 | | | | |
| 45 | | | 2 | | | | | | | | | | |
| 46 | | | | | | | | | | | | | |
| 47 | | | | | | | | | | | | | |
| 48 | | | | | | | | | | | | | |
| 49 | 1.8 | | | | | | | | | | | 1.5 | |
| 50 | | | | | 2.3 | | | | | | | 1.8 | |
| 51 | | | | | | | 2 | | | | | | |
| 52 | | | | | | | | 1.7 | | | | | |
| 53 | | | | | | 1.8 | | | 5 | | | | |
| 54 | | | | | | | | | | | | | |
| 55 | | | | | | | | | | | | | |
| 56 | | | | | | | | | | | | | 0.18 |
| 57 | | | | | | | | | | | | | |
| 58 | | | | 4 | | | | 12.5 | | | | | |
| 59 | | | | | | | | | | | 2 | | |
| 60 | | | | | | 5.2 | | | | | | | |
| 61 | | | | | | | 5.4 | | | 5.1 | | | |
| 62 | 3.5 | | | | | | | | | | 3.5 | | |
| 63 | 3.5 | | | | | | | | | | | | |
| 64 | 5.2 | | 3.5 | | | | | | | | | | 1 |
| 65 | | | | | | 5.3 | 9.1 | | | | | | |
| 66 | 1.7 | | | | | | | 5.3 | | | 1.6 | 3.5 | |
| 67 | | | | | 4 | | 3.6 | | | | | | |
| 68 | | | 3.5 | | 2.4 | | | | | | 3.3 | | |
| 69 | | | | 3.2 | | 3.5 | | | | | | | |
| 70 | | | 1.7 | | | | | | | 1.6 | | | |
| 71 | | | | | | | | | | 4 | 5.1 | | |
| 72 | | | | 5 | | 1.7 | | | | | | | |
| 73 | | | 3.5 | | | | | 3.5 | | | | | |
| 74 | | | | | | | | 8.9 | | | | | |
| 75 | | | | | | | | | 1.9 | | 3.3 | | |
| 76 | 8.6 | 3.6 | | | | | | | | | | 2.4 | 8 |
| 77 | | 3.2 | | | | 3.5 | | 1.7 | | | | | |
| 78 | | | | | | | | | | 5.2 | | | |
| 79 | | | | | | | | 3.5 | | | 8.5 | | |
| 80 | | | | | | | | | | | | | |
| 81 | | | | | | 8.8 | | | | | | | |
| 82 | | | 5.2 | | 5.4 | | | | | 3.5 | | 5.4 | |

TABLE 6-continued

| Perfume compositions | | | | | | | | | | | | | |
|---|---|---|---|---|---|---|---|---|---|---|---|---|---|
| PRM No. | A | B | C | D | E | F | G | H | I | J | K | L | M |
| 83 |  |  |  | 2 |  |  | 1.6 | 3.8 |  |  |  |  |  |
| 84 |  | 2.8 |  | 5.5 | 1.3 |  |  |  |  |  |  |  | 1 |
| 85 |  |  |  |  |  |  | 0.04 |  |  |  |  |  |  |
| 86 |  |  |  |  | 3.2 |  |  |  |  |  |  |  |  |
| 87 | 5.2 |  |  |  |  |  |  |  |  |  |  | 2 |  |
| 88 |  |  |  |  |  |  | 8.6 |  |  |  |  |  |  |
| 89 |  |  |  |  | 1.7 |  |  |  |  |  |  |  |  |
| 90 |  |  |  |  |  |  |  | 0.05 |  |  |  |  |  |
| 91 | 1.7 | 8 |  |  |  |  | 2 |  |  |  |  |  |  |
| 92 |  |  |  |  |  |  |  | 5.3 |  |  |  |  |  |
| 93 |  |  |  | 1.6 |  |  |  |  |  | 1.8 |  |  |  |
| 94 |  |  |  |  | 5 |  | 1.8 |  | 2.5 |  |  |  |  |
| 96 |  |  |  | 0.04 |  | 0.05 |  |  |  |  |  |  |  |
| 97 |  |  | 0.07 |  |  |  |  |  |  | 0.03 |  |  |  |
| 98 | 0.05 |  |  |  |  |  |  |  |  |  | 0.05 | 0.5 | 0.02 |
| 101 |  | 7.2 |  |  |  |  |  |  |  |  |  | 0.5 |  |
| 102 |  |  |  |  |  |  |  | 3.5 |  |  |  |  |  |
| 103 |  |  |  |  |  |  |  |  |  |  |  |  | 1 |
| 104 |  |  |  |  |  |  |  |  |  | 0 | 3.6 |  |  |
| 105 |  | 3.2 |  |  | 1.8 |  |  | 2.3 |  |  | 2 |  |  |
| 107 |  | 2.2 |  |  | 3.5 |  |  | 1.8 |  |  | 2 |  |  |
| 109 |  |  |  |  |  |  |  |  |  |  | 4 |  |  |
| 110 |  | 7.8 |  |  | 2.3 |  |  | 5.6 |  |  | 1.8 |  |  |
| 113 |  | 1.5 |  |  |  |  |  |  |  |  | 3.4 |  |  |
| 114 |  |  | 1.3 |  | 1.5 |  | 3.2 |  | 1.2 | 1.7 |  |  |  |
| 115 |  | 6.8 |  | 1.4 | 3.1 |  |  | 2.5 |  |  | 7.9 |  |  |
| 116 |  | 5.0 |  |  |  |  |  | 5.5 |  |  |  | 20 |  |
| 117 |  |  |  |  |  |  |  |  |  |  |  | 0.4 |  |
| 118 |  |  |  |  |  |  |  |  |  |  |  | 1 |  |
| 119 |  |  |  |  |  |  |  |  |  |  |  | 19.2 |  |
| 120 |  |  |  |  |  |  |  |  |  |  |  | 14 |  |
| 121 |  |  |  |  |  |  |  |  |  |  |  | 12 |  |
| 122 |  |  |  |  |  |  |  |  |  |  |  | 6 |  |
| 123 |  |  |  |  |  |  |  |  |  |  |  |  |  |
| 124 |  |  |  |  | 2 |  |  |  |  |  |  |  |  |

Example 1 a) Synthesis of 4,4'-Bis(chlorocarbonyl)azobenzene which is also known as azobenzene-4,4'-dicarbonyl dichloride.

15 grams of 4-nitrobenzoic acid (CAS 62-23-7) and 50 grams of sodium hydroxide are mixed in 225 mL of demineralised water and are heated to 70° C. until the solid is completely dissolved. Then, a hot aqueous glucose solution (100 grams, of glucose in 150 mL water) is slowly added at 70° C., whereupon a yellow precipitate is obtained. A stream of air is passed into the mixture for 5 hours and a light brown precipitate is obtained. This precipitate is filtered, dissolved in 20 mL of demineralised water and acidified with 25 mL acetic acid, thus: yielding azobenzene-4,4'-dicarboxylic acid as a light pink precipitate. This precipitate is filtered, washed with 1000 mL of demineralised water and dried in oven at 100° C. for 48 h. The azobenzene 4,4'-dicarboxylic acid thus obtained (9.0 g) and 17.5 g of $PCl_5$ are mixed in 145 ml 1,2-dichloroethane at 0° C. The mixture is than refluxed for 2 hours at 80° C. under $N_2$ atmosphere. The obtained bright red crystals are filtered and recrystallized one or more times from toluene.

b) Preparation of Microcapsules.

In order to obtain microcapsules a first solution is prepared by dissolving 0.25 grams of Polyvinyl alcohol (Mowiol®18-88, $M_w$~130,000 available from Fluka) in 25 ml of demineralized water at 40° C. and 500 rpm. Then, a second solution is prepared by dissolving 0.25 grams of azobenzene-4,4'-dicarbonyl dichloride (A1575, TCI) and 0.024 grams of 1,3,5-benzenetricarbonyl trichloride (147532, Aldrich), previously melted, in 12.5 ml of a Perfume Composition such as the ones described above in Table 6 at 25° C. A third solution is then prepared by dissolving 0.237 grams of 1,8-diaminoctane (D22401, Aldrich), previously melted, in 12.5 mL demi-water containing 0.125 grams of Polyvinyl alcohol (Mowiol® 18-88, $M_w$~130,000 available from Fluka). Then, a first composition is prepared by emulsifying the second solution into the first solution at 1,200 rpm for 20 minutes at 25° C. using an IKA RW20 mixer. Then, the third solution is added drop wise into the dispersion during 10 minutes and encapsulation is achieved by mixing this second composition at 300 rpm for 90 minutes at 0° C. to form perfume polyamide microcapsules. 200 mL of a sodium sulfate aqueous solution (6 grams of sodium sulfate (238597, Sigma-Aldrich) are dissolved in 194 mL demineralized water) are added to this second composition. This composition is used without further treatment. The level of perfume based on total weight composition in the composition is 5.4%.

Example 2

The procedure is analogous to Example 1 except that the longer time of the polycondensation reaction is 180 minutes rather than 90 minutes.

% free perfume in the composition after making the encapsulates: 0.36%

Example 3

The procedure is analogous to Example 2 except that the lower temperature of the polycondensation reaction is performed at 10° C. rather than at 20° C., so longer reaction time is required up to 240 minutes.

% free perfume in the composition (based on total weight composition) after making the encapsulates: 0.56%

Example 4 (Cap. 4)

The procedure is analogous to Example 1 except that the higher temperature of the polycondensation reaction is performed at 22° C. rather than at 0° C.

% free perfume in the composition (based on total weight composition) after making the encapsulates: 0.36%

Example 5 (Cap. 1), Example 6 (Cap. 2), Example 7 (Cap. 3)

The procedures is analogous to Example 1 except that the composition is different (see Table 7): amounts of 1,3,5-benzenetricarbonyl trichloride added in the first composition are variable, the amount of 1,8-diaminooctane in the second solution is 0.123 grams rather than 0.237 grams, moreover additionally 0.143 grams of sodium hydrogen carbonate are added to said second solution.

The polycondensation reaction is performed at 20° C.

place of 1,3,5-benzene tricarbonyl trichloride. Sodium hydrogen carbonate in the second solution is 0.168 grams. The polycondensation reaction is performed at 40° C.

Example 12

Procedure is similar to Example 7, except 0.011 grams 1,2,4-benzenetriamine dihydrochloride (available from TCI America) is used in place of 1,3,5-benzene tricarbonyl chloride. The polycondensation reaction is performed at 40° C.

Example 13

Procedure is similar to Example 12, except 0.047 grams 1,2,4-benzenetriamine dihydrochloride is used.

Example 14

Procedure is similar to Example 12, except 0.060 grams 1,2,4-benzenetriamine dihydrochloride is used.

Example 15

Procedure is similar to Example 12, except 0.100 grams 1,2,4-benzenetriamine dihydrochloride is used.

TABLE 7

| | monomers amounts | | | | | | | |
|---|---|---|---|---|---|---|---|---|
| | First solution | | Second solution | | | Third solution | | |
| | Water (mL) | PVA (g) | Perfume composition (mL) | Azo (g) | TriCl (g) | Water (mL) | PVA (g) | 1,8diamine (g) | BC (g) |
| Example 5 | 25 | 0.25 | 12.5 | 0.25 | 0.0067 | 12.5 | 0.125 | 0.123 | 0.143 |
| Example 6 | 25 | 0.25 | 12.5 | 0.25 | 0.0335 | 12.5 | 0.125 | 0.123 | 0.143 |
| Example 7 | 25 | 0.25 | 12.5 | 0.25 | 0.0674 | 12.5 | 0.125 | 0.123 | 0.143 | wherein:
Azo: azobenzene-4,4'-dicarbonyl dichloride
TriCl: 1,3,5-benzenetricarbonyl trichloride
1,8diamine: 1,8-diaminooctane
BC: sodium hydrogen carbonate
PVA: polyvinyl alcohol
% free perfume in the composition (based on total weight composition) after making the encapsulates: Example 6: 0.2%

Example 8

This procedure is similar to Example 6, except 0.28 grams of p-Phenylenediamine (78429, Aldrich) is used instead of 1,8-diaminooctane. The polycondensation reaction is performed at 40° C. rather than 20° C. and during 12 hours instead of 90 minutes.

Example 9

Procedure is similar to Example 8, except cyanuric chloride (98620, Fluka) is used in place of 1,3,5-benzene tricarbonyl chloride. The polycondensation reaction is performed at 22° C.

Example 10

Procedure is similar to Example 1, except 0.394 grams of 2-(4,5-diamino-1H-pyrazol-1-yl)ethanol sulfate (RODOL HDAP, available from Qingdao Kepuway Chemical Co., Ltd.) is used in place of 1,8-diaminooctane. The polycondensation reaction is performed at 0° C.

Example 11

Procedure is similar to Example 7, except 0.017 grams cyanuric chloride (available from Sigma-Aldrich) is used in Example 16

Procedure is similar to Example 7, except the amount of 1,8-diaminooctane is reduced to 0.082 grams, 0.031 grams of 1,4-diaminobenzene are added to the second solution and 0.150 grams 1,3,5-benzene tricarbonyl chloride are used. The polycondensation reaction is performed at 22° C.

Example 17

Procedure is similar to Example 9, except 0.050 grams cyanuric chloride is used.

Example 18

Procedure is similar to Example 9, except 0.011 grams 1,2,4-benzenetriamine dihydrochloride are used in place of cyanuric chloride. The polycondensation reaction is performed at 22° C.

Example 19

Procedure is similar to Example 18, except 0.016 grams 1,2,4-benzenetriamine dihydrochloride are used.

Example 20

Procedure is similar to Example 18, except 0.055 grams 1,2,4-benzenetriamine dihydrochloride are used.

Example 21

Procedure is similar to Example 18, except 0.100 grams 1,2,4-benzenetriamine dihydrochloride are used.

Example 22

Procedure is similar to Example 12, except 0.163 grams of RODOL HDAP are used in place of the 1,8-diaminooctane. The polycondensation reaction is performed at 22° C.

Example 23

Procedure is similar to Example 22, except 0.016 grams 1,2,4-benzenetriamine dihydrochloride are used.

Example 24

Procedure is similar to Example 22, except 0.032 grams 1,2,4-benzenetriamine dihydrochloride are used.

Example 25

Procedure is similar to Example 6, except 56.35 grams of an aqueous solution (6 grams sodium sulfate (238597, Sigma-Aldrich) and 0.35 grams of Xantham Gum (Kelzan ASX-T, CP Kelco) are dissolved in 50 mL demineralized water) is used instead of 200 mL of a sodium sulfate aqueous solution. 25.002 grams of said composition prepared by this Example 25 are exposed to UV-light as described in test method (9) Measurement of released perfume in the encapsulate suspension after exposure to light, obtaining following results:

| | % perfume, based on total weight composition |
|---|---|
| % free perfume in the composition after making the encapsulates | 0.37 |
| % perfume after 3 hours of exposure to UV-light | 2.09 |
| % perfume after 3 hours UV-light + 24 hours in the darkness | 0.69 |
| % perfume after 3 hours UV-light + 24 hours in the darkness + 3 hours UV-light | 1.72 |
| % perfume after 3 weeks in the darkness | 0.46 |

Thus, capsules are able to open with the light and close again after the light trigger is removed to avoid additional the perfume release.

Example 26

Procedure is similar to Example 25 except 0.51 grams 1,2-ethanediamine (Sigma-Aldrich) are used in place of the 1,8-diaminooctane. 25.037 grams of said composition prepared by this Example 26 are exposed to UV-light as described in test method (9) Measurement of released perfume in the encapsulate suspension after exposure to light, obtaining following results:

| | % perfume, based on total weight composition |
|---|---|
| % perfume in the composition | 15.1 |
| % free perfume in the composition after making the encapsulates | 0.73 |
| % perfume after 3 hours of exposure to UV-light | 1.94 |
| % perfume after 3 hours UV-light + 24 hours in the darkness | 1.12 |
| % perfume after 3 hours UV-light + 24 hours in the darkness + 3 hours UV-light | 1.15 |
| % perfume after 3 weeks in the darkness | 1.17 |

Thus, using this process, once capsules open with the light, there is a continuous release even in the darkness and further exposure to light is not needed to maintain the release of the perfume composition. Data after 3 weeks shows that the cross-linking of the shell is not adequate, since the perfume composition is leaking out of the capsule.

Example 27

Procedure is similar to Example 25 except 0.75 grams 1,4-diaminobutane (Sigma-Aldrich) are used in place of the 1,8-diaminooctane. 25.006 grams of said composition are exposed to UV-light as described in test method (9) Measurement of released perfume in the encapsulate suspension after exposure to light, obtaining following results:

| | % perfume, based on total weight composition |
|---|---|
| % perfume in the composition | 15.4 |
| % free perfume in the composition after making the encapsulates | 0.35 |
| % perfume after 3 hours of exposure to UV-light | 2.59 |
| % perfume after 3 hours UV-light + 24 hours in the darkness | 1.34 |
| % perfume after 3 hours UV-light + 24 hours in the darkness + 3 hours UV-light | 4.82 |

Thus, examples 25, 26 and 27 teach us that the carbon chain length of the diamine may be key in order to obtain the right balance between stability and release, so short carbon chains do not provide the right stability profile or the proper release profile, while long carbon chains do. Combining encapsulates containing different carbon chain lengths provides the right balance between stability and release upon time and electromagnetic radiation.

Example 28

Procedure is similar to Example 4 except 56.35 grams of an aqueous solution (6 grams sodium sulfate (238597, Sigma-Aldrich) and 0.35 grams of Xantham Gum (Kelzan ASX-T, CP Kelco) are dissolved in 50 mL demineralized water) is used instead of 200 mL of a sodium sulfate aqueous solution. 25.037 grams of said composition are exposed to UV-light as described in test method (9) Measurement of released perfume in the encapsulate suspension after exposure to light, obtaining following results:

|  | % perfume, based on total weight composition |
| --- | --- |
| % perfume in the composition | 15.3 |
| % free perfume in the composition after making the encapsulates | 0.42 |
| % perfume after 3 hours of exposure to UV-light | 4.04 |
| % perfume after 3 hours UV-light + 24 hours in the darkness | 0.4 |
| % perfume after 3 hours UV-light + 24 hours in the darkness + 3 hours UV-light | 0.57 |
| % perfume after 3 weeks in the darkness | 0.61 |

The amount of free amine in the composition may be important since this free amine might react in the interface of the perfume upon porosity increase due to exposure to electromagnetic radiation.

Example 29

Procedure is similar to Example 25 except 0.0615 grams 1,8-diaminooctane and 0.026 grams 1,2-ethanediamine are used. % free perfume in the composition (based on total weight composition) after making the encapsulates: 0.47%

Example 30

Procedure is similar to Example 25 except 0.092 grams 1,8-diaminooctane and 0.023 grams p-Phenylenediamine (78429, Aldrich) are used. % free perfume in the composition (based on total weight composition) after making the encapsulates: 0.51%.

Example 31

Procedure is similar to Example 25 except 0.074 grams 1,4-butanediol are used in place of the 1,8-diaminooctane. % free perfume in the composition (based on total weight composition) after making the encapsulates: 1.32%.

Example 32

Olfactive Evaluation Comparative Example in All-Purpose Cleaner Composition

| % Weight | 32REF | 32A | 32B | 32C | 32D |
| --- | --- | --- | --- | --- | --- |
| C9-C11 EO8 (Neodol 91-8 ®) | 4 | 4 | 4 | 4 | 4 |
| Sodium Hydroxide | 0.16 | 0.16 | 0.16 | 0.16 | 0.16 |
| Koralone | 0.05 | 0.05 | 0.05 | 0.05 | 0.05 |
| Citric Acid | 0.6 | 0.6 | 0.6 | 0.6 | 0.6 |
| Polysaccharide (Xanthan Gum, Keltrol CG-SFT ® Kelco) | 0.25 | 0.25 | 0.25 | 0.25 | 0.25 |
| Perfume | 0.5 | | | | |
| Encapsulates as disclosed in Example 4 | | | | | 9.3 |
| Encapsulates as disclosed in Example 5 | | 9.3 | | | |
| Encapsulates as disclosed in Example 6 | | | 9.3 | | |
| Encapsulates as disclosed in Example 7 | | | | 9.3 | |
| DTPA | 0.25 | 0.25 | 0.25 | 0.25 | 0.25 |
| Water | Balance | Balance | balance | Balance | Balance |

| Olfactive Evaluation (test method 7) | Olfactive Evaluation after 30 min | Olfactive Evaluation after 120 min | Olfactive Evaluation after 210 min | Olfactive Evaluation after 360 min |
| --- | --- | --- | --- | --- |
| Free perfume 32A | 73% | 73% | 62% | 63% |
| 32A | 27% | 27% | 38% | 37% |
| Free perfume 32B | 14% | 19% | 37% | 32% |
| 32B | 86% | 81% | 63% | 68% |
| Free perfume 32C | 70% | 47% | 48% | 38% |
| 32C | 30% | 53% | 52% | 62% |
| Free perfume 32D | 43% | 48% | 48% | 52% |
| 32D | 57% | 52% | 52% | 48% |

Example 33

Headspace Evaluation in Fabric Refresher Compositions

Following compositions have been evaluated using test method (6) Headspace Evaluation of Capsules in Hard Surface Applications

|  | 33REF | 33A | 33B | 33C | 33D |
| --- | --- | --- | --- | --- | --- |
| Polysaccharide (Xanthan Gum, Keltrol CG-SFT ® Kelco) | 0.1 | 0.1 | 0.1 | 0.1 | 0.1 |
| Lupasol WF CAS 9002-98-6 | 0.07 | 0.07 | 0.07 | 0.07 | 0.07 |
| Diethylene Glycol | 0.175 | 0.175 | 0.175 | 0.175 | 0.175 |
| Perfume | 0.49 | | | | |
| Encapsulates as disclosed in Example 4 | | | | | 9.1 |
| Encapsulates as disclosed in Example 5 | | 9.1 | | | |
| Encapsulates as disclosed in Example 6 | | | 9.1 | | |
| Encapsulates as disclosed in Example 7 | | | | 9.1 | |

| | | | | | |
|---|---|---|---|---|---|
| Hydroxypropyl Beta CD | 0.63 | 0.63 | 0.63 | 0.63 | 0.63 |
| Basophor ELH 60 | 0.05 | 0.05 | 0.05 | 0.05 | 0.05 |
| Uniquat 2250 | 0.06 | 0.06 | 0.06 | 0.06 | 0.06 |
| Silwet L-7600 | 0.1 | 0.1 | 0.1 | 0.1 | 0.1 |
| Citric Acid | 0.015 | 0.015 | 0.015 | 0.015 | 0.015 |
| Maleic Acid CAS 110-16-7 | 0.05 | 0.05 | 0.05 | 0.05 | 0.05 |
| Koralone B-119 | 0.015 | 0.015 | 0.015 | 0.015 | 0.015 |
| Ethanol | 3 | 3 | 3 | 3 | 3 |
| Water | Balance | Balance | Balance | Balance | Balance |

| Headspace Evaluation under fluorescent light (test method 6) | Headspace Evaluation after 1 hour | Headspace Evaluation after 6 hours | Headspace Evaluation after 24 hours |
|---|---|---|---|
| Free perfume | 157 | 59 | 31 |
| 33A | 250 | 83 | 55 |
| 33B | 215 | 77 | 58 |
| 33C | 182 | 60 | 45 |
| 33D | 180 | 65 | 48 |

Thus, composition A provides a blooming effect just after the application and release over 24 hours under fluorescent light source.

The azo benezene moiety can be incorporated into acrylate/vinyl copolymer systems Example 34

Synthesis of Divinyl azobenzene 5 grams of 4-nitro-styrene (available from Polysciences), 5.35 grams of sodium hydroxide (Sigma-Aldrich, 1M solution) and 50 ml of isopropanol (Sigma-Aldrich) are added to a round bottom flask. 4.4 grams of zinc dust (Sigma-Aldrich) is added slowly (over 45 minutes), and the solution is refluxed 7 hrs. The reaction mixture is cooled to RT, filtered through a Celite pad and the alcohol is distilled off. 1N HCl is added to acidify the mixture and the solids are extracted into $Et_2O$ (3×100 mL) and washed with 0.1N HCl. The organic layer is then washed with brine, dried ($Na_2SO_4$), and the solvent removed in vacuum. The residue is purified by column chromatography ($SiO_2$/90-10 hex-$CH_2Cl_2$) to provide the product as a red solid (1.82 grams).

Example 35

4-methacryloxy-azobenzene Synthesis

To a solution of 4-hydroxy-azobenzene (10 grams, Sigma-Aldrich) in $CH_2Cl_2$ (400 mL) under nitrogen 14.7 mL diisopropylethylamine (Sigma-Aldrich) and 100 mg 4-dimethylaminopyridine (Sigma-Aldrich) are added. The solution is cooled to 0° C., and 6.7 mL methacryoyl chloride is added dropwise over 30 minutes. The reaction is warmed to RT and stirred 18 h. 100 mL of a 1N HCl solution (Sigma-Aldrich) are added and the layers are separated. The organic layer is washed with brine, dried ($Na_2SO_4$) and concentrated in vacuum. The resulting solid is triturated with hexanes, then filtered and dried 24 h at RT. Yield obtained: 10.2 grams.

Example 36

4,4'-dimethacryloxy-azobenzene Synthesis

To a solution of 5.37 grams of 4,4'-dihydroxy-azobenzene (Princeton Building Blocks, Princeton, N.J.) in dichloromethane (200 mL) under nitrogen atmosphere is added 20 mL of diisopropylethylamine. The solution is cooled to 0° C. and 50 mg 4-dimethylaminopryridine is added. A solution of methacryoyl chloride (5.75 mL) is added dropwise over 30 minutes and the solution is warmed to RT and stirred 24 h. 1N HCl is added and the layers are separated. The organic layer is washed with brine, dried ($Na_2SO_4$) and the solvent is removed in vacuum to provide the product (6.4 grams).

Example 37

4-hydroxymethyl azobenzene Synthesis

To a solution of 4-amino benzyl alcohol (7.5 grams) in ethanol (100 mL) is added nitroso benzene (6.52 grams). To this solution is added acetic acid (6 mL) and the solution is heated to 40° C. for 4 h. The solution is cooled to RT and the solvent is removed in vacuum. The residue is triturated with hexanes (5×100 mL) and the solid is filtered and dried to provide the diazo benzene product (10.12 grams).

Example 38

4-methacryloxymethyl-azobenzene

To a solution of 4-hydroxymethyl azobenzene (5 grams) in $CH_2Cl_2$ (150 mL) under nitrogen is added 10 mL of diisopropylethylamine. The solution is cooled to 0° C. and 25 mg of 4-dimethylaminopyridine is added. A solution of methacryloyl chloride (2.85 mL) is added dropwise over 30 minutes and the reaction is stirred overnight at room temperature. 1 N HCl is added and the layers are separated. The organic layer is washed with brine, dried ($Na_2SO_4$) and the solvent is removed in vacuum to provide the product (4.8 grams).

Example 39

4,4'-dimethacryloxymethyl-azobenzene

To a solution of 10 grams 4,4'-dihydroxymethyl azobenzene (Angene International Ltd., Hong Kong) in $CH_2Cl_2$ (400 mL) is added 30 mL diisopropylethylamine and 100 mg 4-dimethylaminopyridine. The reaction is cooled to 0° C. and 6 mL methacryloyl chloride is added dropwise over 30 minutes. The reaction is warmed to RT and stirred overnight. 1 N HCl is added and the layers are separated. The organic layer is washed with brine, dried ($Na_2SO_4$) and the solvent is removed in vacuo to provide the product (7.7. grams).

Example 40

4,4'-di(methacrylamido)-azobenzene Synthesis

To a solution of 4,4'-diamino-diazobenzene (5 grams, prepared according to Organic Syntheses Coll. Vol. 5, p. 341) in CH2Cl2 (200 mL) is added 14.1 mL of diisopropylethylamine and 25 mg of 4-dimethylaminopyridine. The solution is cooled to 0° C. and methacryloyl chloride (5.75 mL) is added over 30 minutes. The reaction is warmed to RT and stirred 24 h. The resulting precipitate is filtered off, washed with water (3×50 mL) and then with methanol (3×75 mL). The solid is dried overnight in a vacuum oven at RT (5.4 grams).

Example 41 di-Aldehyde Functional diazobenzene Synthesis a) 4,4'-dibromoazobenzene Synthesis 50 g of p-bromoaniline (available from Sigma-Aldrich) and 1 liter of anhydrous benzene is added to a round bottom flask with stirring. 258 grams of finely powdered lead tetraacetate is added slowly over 3 hours. After one additional hour the lead diacetate is filtered off and the filtrate is washed thoroughly with 3 liters of water. After separating the benzene and aqueous layers, the benzene solution is concentrated to a volume of 100 ml. The concentrate on cooling in ice yields 31 g. of a solid material that on sublimation in vacuum (0.001 mm.) within the temperature range of 200-250" (airbath) gives 20 grams of 4,4'-dibromoazobenzene. The product is recrystallized from chloroform.

b) di-Aldehyde Functional diazobenzene Synthesis

A solution of 10 grams of 4,4'-dibromo-azobenzene from the example above and 50 ml of diethyl ether (available from Sigma-Aldrich) is added dropwise to a dispersion of 2 grams of magnesium (available from Sigma-Aldrich) in 25 ml of diethyl ether in a round bottom flask equipped with nitrogen gas. After 3 hours at 25 C., a solution of 3 grams of paraformaldehyde (available from Sigma-Aldrich) dissolved in 30 ml of diethyl ether is added dropwise over a 30 minute period. After stirring for an additional 8 hours, the solution is acidified with an aqueous solution of 0.1N HCl (available from Sigma-Aldrich). The ether solution is filtered from the solids and extracted with 0.1N sodium bicarbonate solution, followed by extractions with water. The ether layer is vacuum dried and 2 grams of the product is dissolved into 50 ml of acetonitrile. A solution of 5 grams of sodium periodate (NaIO4) in 10 milliliters of water and this is added to the product from the previous step dissolved in acetonitrile. The reaction mixture is diluted with 200 mL of methylene chloride and filtered. The resin is thoroughly washed with methylene chloride and combined washings and filtrates are purified on silica-gel plates or silica-gel column. IR and 1H NMR spectral data confirm the identity of the product.

Example 42

Acrylate Encapsulates Preparation with Divinyl Azobenzene

An oil solution, consisting of 56 grams perfume composition as described in Table 6, 37 grams Isopropylmyristate, 0.5 grams DuPont Vazo-67, 0.125 grams tertiarybutylaminoethyl methacrylate, 0.125 g 2-carboxyethyl acrylate, and 6.38 g Sartomer CN975 (hexafunctional-acrylate oligomer) and 4.00 grams of Divinyl azobenzene (from Example 34) is added to a 55° C. temperature controlled steel jacketed reactor, with mixing at 550 rpm (4 tip, 2" diameter, flat mill blade) and a nitrogen blanket applied at 100 cc/min. The oil solution is heated to 75° C. in 45 minutes, held at 75° C. for 45 minutes. Mixing is stopped and a water solution, consisting of 100 grams demineralized water, 14 g 5% Selvol 540 polyvinyl alcohol, 3.250 g 1N NaOH, 1 g 4,4'-Azobis (4-cyanovaleric acid), is added to the bottom of the oil solution, using a funnel. Mixing is again started, at 2,500 rpm, for 60 minutes to emulsify the oil phase into the water solution. After milling is completed, mixing is continued with a 3" propeller at 350 rpm. The temperature is increased to 75° C. in 45 minutes, held at 75° C. for 4 hours, heated to 90° C. in 30 minutes and held at 90° C. for 2 hours. The batch is then allowed to cool to room temperature. The finished microcapsules have a median particle size of 7 microns, and a broadness index of 1.3. 25 grams of said composition prepared by this Example are exposed to UV-light for 4 hours as described in test method (9) Measurement of released perfume in the encapsulate suspension after exposure to light, obtaining following results:

|  | % perfume, based on total weight composition |
| --- | --- |
| % free perfume in the composition after making the encapsulates | 1.2 |
| % perfume after 4 hours of exposure to UV-light | 11.2 |

Thus, capsules are able to open with the light and release the perfume.

Example 43

Acrylate Encapsulates Preparation with di-Methacrylamido Azobenzene

An oil solution, consisting of 56 grams of a perfume composition as described in Table 6, 37 grams Isopropylmyristate, 0.5 grams DuPont Vazo-67, 0.125 grams tertiarybutylaminoethyl methacrylate, 0.125 grams 2-carboxyethyl acrylate, and 1.92 grams Sartomer CN975 (hexafunctional-acrylate oligomer) and 1.28 grams of dimethacrylamide-azobenzene (from Example 40) is added to a 55° C. temperature controlled steel jacketed reactor, with mixing at 550 rpm (4 tip, 2" diameter, flat mill blade) and a nitrogen blanket applied at 100 cc/min. The oil solution is heated to 75° C. in 45 minutes, held at 75° C. for 45 minutes. Mixing is stopped and a water solution, consisting of 100 grams demineralized water, 14 grams 5% Selvol 540 polyvinyl alcohol, 3.250 grams 1N NaOH, 1 grams 4,4'-Azobis (4-cyanovaleric acid), is added to the bottom of the oil solution, using a funnel. Mixing is again started, at 2,500 rpm, for 60 minutes to emulsify the oil phase into the water solution. After milling is completed, mixing is continued with a 3" propeller at 350 rpm. The temperature is increased to 75° C. in 45 minutes, held at 75° C. for 4 hours, heated to 90° C. in 30 minutes and held at 90° C. for 2 hours. The batch is then allowed to cool to room temperature. The finished microcapsules have a median particle size of 7 microns, and a broadness index of 1.3. 25 grams of said composition prepared by this Example are exposed to UV-light for 4.5 hours as described in test method (9) Measurement of released perfume in the encapsulate suspension after exposure to light, obtaining following results:

|  | % perfume, based on total weight composition |
| --- | --- |
| % free perfume in the composition after making the encapsulates | 2.5 |
| % perfume after 4.5 hours of exposure to UV-light | 9.3 |

Thus, capsules are able to open with the light and release the perfume.

Example 44

Acrylate Encapsulates Preparation with Methacryloxy Azobenzene

An oil solution, consisting of 56 grams Perfume composition as described in Tale 6, 37 grams Isopropylmyristate, 0.5 grams DuPont Vazo-67, 0.125 grams tertiarybutylaminoethyl methacrylate, 0.125 grams 2-carboxyethyl acrylate, and 8.034 grams Sartomer CN975 (hexafunctional-acrylate oligomer) and 4.88 grams of methacryloxy-azobenzene (from Example 35) is added to a 55° C. temperature controlled steel jacketed reactor, with mixing at 550 rpm (4 tip, 2" diameter, flat mill blade) and a nitrogen blanket applied at 100 cc/min. The oil solution is heated to 75° C. in 45 minutes, held at 75° C. for 45 minutes. Mixing is stopped and a water solution, consisting of 100 grams demineralized water, 14 grams 5% Selvol 540 polyvinyl alcohol, 3.250 g 1N NaOH, 1 grams 4,4'-Azobis (4-cyanovaleric acid), is added to the bottom of the oil solution, using a funnel. Mixing is again started, at 2,500 rpm, for 60 minutes to emulsify the oil phase into the water solution. After milling is completed, mixing is continued with a 3" propeller at 350 rpm. The temperature is increased to 75° C. in 45 minutes, held at 75° C. for 4 hours, heated to 90° C. in 30 minutes and held at 90° C. for 2 hours. The batch is then allowed to cool to room temperature. The finished microcapsules have a median particle size of 7 microns, and a broadness index of 1.3.

Example 45

Acrylate Encapsulates Preparation with 4,4'-dimethacryloxy-azobenzene

An oil solution, consisting of 56 grams Perfume composition, 37 grams Isopropylmyristate, 0.5 grams DuPont Vazo-67, 0.125 grams tertiarybutylaminoethyl methacrylate, 0.125 grams 2-carboxyethyl acrylate, and 5.75 grams Sartomer CN975 (hexafunctional-acrylate oligomer) and 4 grams of 4,4'-dimethacryloxy-azobenzene (from Example 38) is added to a 55° C. temperature controlled steel jacketed reactor, with mixing at 550 rpm (4 tip, 2" diameter, flat mill blade) and a nitrogen blanket applied at 100 cc/min. The oil solution is heated to 75° C. in 45 minutes, held at 75° C. for 45 minutes. Mixing is stopped and a water solution, consisting of 100 grams Water, 14 grams 5% Selvol 540 polyvinyl alcohol, 3.25 grams 1N NaOH, 1 grams 4,4'-Azobis (4-cyanovalericacid), is added to the bottom of the oil solution, using a funnel. Mixing is again started, at 2,500 rpm, for 60 minutes to emulsify the oil phase into the water solution. After milling is completed, mixing is continued with a 3" propeller at 350 rpm. The temperature is increased to 75° C. in 45 minutes, held at 75° C. for 4 hours, heated to 90° C. in 30 minutes and held at 90° C. for 2 hours. The batch is then allowed to cool to room temperature. The finished microcapsules have a median particle size of 7 microns, and a broadness index of 1.3.

Example 46

Acrylate Encapsulates Preparation with 4,4'-dimethacryloxy methyl-azobenzene An oil solution, consisting of 56 grams Perfume composition as described in Table 6, 37 grams Isopropylmyristate, 0.5 grams DuPont Vazo-67, 0.125 grams tertiarybutylaminoethyl methacrylate, 0.125 grams 2-carboxyethyl acrylate, and 6 grams Sartomer CN975 (hexafunctional-acrylate oligomer) and 4 grams of 4,4'-dimethacryloxy methyl-azobenzene (from Example 36) is added to a 55° C. temperature controlled steel jacketed reactor, with mixing at 550 rpm (4 tip, 2" diameter, flat mill blade) and a nitrogen blanket applied at 100 cc/min. The oil solution is heated to 75° C. in 45 minutes, held at 75° C. for 45 minutes. Mixing is stopped and a water solution, consisting of 100 grams demineralized water, 14 grams 5% Selvol 540 polyvinyl alcohol, 3.250 g 1N NaOH, 1 grams 4,4'-Azobis (4-cyanovalericacid), is added to the bottom of the oil solution, using a funnel. Mixing is again started, at 2,500 rpm, for 60 minutes to emulsify the oil phase into the water solution. After milling is completed, mixing is continued with a 3" propeller at 350 rpm. The temperature is increased to 75° C. in 45 minutes, held at 75° C. for 4 hours, heated to 90° C. in 30 minutes and held at 90° C. for 2 hours. The batch is then allowed to cool to room temperature. The finished microcapsules have a median particle size of 7 microns, and a broadness index of 1.3.

Example 47

Agglomeration of Encapsulates

A 9 kg aliquot of perfume microcapsule slurry of example 1 (after phase split, only capsules are used for the agglomeration process) is mixed using a Eurostar mixer (IKA) with a R1382 attachment at a constant speed of 200 rpm. To the aliquot 500 grams of carboxymethyl cellulose (CP Kelco) is added while mixing using the Eurostar mixer with same attachment and speed as described above. The slurry is mixed for a total of two hours or until a uniform paste is formed. 1.28 kg of precipitated silica Sipernat® 22S (Degussa) is added to a F-20 paddle mixer (Forberg). The mixer is run initially for 5 seconds to distribute the silica evenly on the base of the mixer. The mixer is stopped and 8.25 kg of paste, is evenly distributed onto the powder. The mixer is then run at 120 rpm for a total of 30 seconds. Following mixing, the wet particles are dumped out of the mixer and screened using a 2,000 micron sieve to remove the oversize. The product passing through the screen is dried in 500 grams batches in a CDT 0.02 fluid bed dryer (Niro) to a final moisture content of 20 wt % measured by Karl Fischer. The dryer is operated at an inlet temperature of 140° C. and air velocity of 0.68 m/s.

Examples 48

Examples of Laundry Detergent Compositions Comprising the Perfume Composition are Included Below

| Raw material | % w/w of laundry detergent compositions | | | | | | | |
| --- | --- | --- | --- | --- | --- | --- | --- | --- |
| | 48A | 48B | 48C | 48D | 48E | 48F | 48G | 48H |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |

-continued

| Raw material | % w/w of laundry detergent compositions | | | | | | | |
|---|---|---|---|---|---|---|---|---|
| | 48A | 48B | 48C | 48D | 48E | 48F | 48G | 48H |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Encapsulates of Example 4 | 10 | 6 | — | 11.3 | 7 | 1 | 5 | 7 |
| Encapsulates of Example 6 | — | 4 | 8.5 | — | 3 | 9 | 5 | — |
| Water & Miscellaneous | Balance to 100% | | | | | | | |

The equipment and materials described in Examples 6 through to 21 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA Examples 49

Fabric Conditioner

Non-limiting examples of fabric conditioners containing the polymer coated perfume microcapsules disclosed in the present specification are summarized in the following table.

| (% wt) | EXAMPLES | | | | | | | | | |
|---|---|---|---|---|---|---|---|---|---|---|
| | 49A | 49B | 49C | 49D | 49E | 49F | 49G | 49H | 49I | 49J |
| FSA[a] | 14 | 16.47 | 14 | 12 | 12 | 16.47 | — | — | 5 | 10 |
| FSA[b] | — | — | — | — | — | — | 3.00 | — | — | — |
| FSA[c] | — | — | — | — | — | — | — | 6.5 | — | — |
| Ethanol | 2.18 | 2.57 | 2.18 | 1.95 | 1.95 | 2.57 | — | — | 0.81 | — |
| Isopropyl Alcohol | — | — | — | — | — | — | 0.33 | 1.22 | — | 1.0 |
| Starch[d] | 1.25 | 1.47 | 2.00 | 1.25 | — | 2.30 | 0.5 | 0.70 | 0.71 | 0.42 |
| Phase Stabilizing Polymer[f] | 0.21 | 0.25 | 0.21 | 0.21 | 0.14 | 0.18 | 0.15 | 0.14 | 0.2 | 0.1 |
| Suds Suppressor[g] | — | — | — | — | — | — | — | 0.1 | — | — |
| Calcium Chloride | 0.15 | 0.176 | 0.15 | 0.15 | 0.30 | 0.176 | — | 0.1-0.15 | — | 0025. |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |

-continued

| (% wt) | EXAMPLES | | | | | | | | | |
|---|---|---|---|---|---|---|---|---|---|---|
| | 49A | 49B | 49C | 49D | 49E | 49F | 49G | 49H | 49I | 49J |
| HCl | 0.012 | 0.014 | 0.012 | 0.012 | 0.028 | 0.028 | 0.016 | 0.025 | 0.011 | 0.011 |
| Encapsulates as disclosed in Example 4 | 5 | 6.2 | 4 | 5.5 | 3 | — | 1 | — | — | — |
| Encapsulates as disclosed in example 5 | — | — | 1 | — | 1.5 | — | 0.5 | — | 0.5 | — |
| Encapsulates as disclosed in example 25 | — | — | — | — | — | 2 | 1.8 | 3 | 2.3 | 2.5 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Rheovis DCE ex BASF.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
† balance

Examples 50

Liquid and Gel Detergents

| Ingredients | (% by Weight) | | |
|---|---|---|---|
| | 50A | 50B | 50C |
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Encapsulates as Example 25 | 2 | 2.5 | 1.8 |
| Water | 22.1 | 50.8 | 2.9 |
| Perfume, dyes, miscellaneous minors | Balance | Balance | Balance |
| Undiluted viscosity ($V_n$) at 20 s$^{-1}$, cps | 2,700 | 400 | 300 |

Example 51

Liquid Unit Dose

The following are examples of unit dose executions wherein the liquid composition is enclosed within a PVA film. The preferred film used in the present examples is Monosol M8630 76 µm thickness.

| | 51D 3 compartments | | | 51E 2 compartments | | 51F 3 compartments | | |
|---|---|---|---|---|---|---|---|---|
| Compartment # | A | B | C | D | E | F | G | H |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |

-continued

| | 51D 3 compartments | | | 51E 2 compartments | | 51F 3 compartments | | |
|---|---|---|---|---|---|---|---|---|
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| Enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | 0.4 | | | |
| Brightener | 0.2 | 0.2 | 0.2 | 0.3 | | 0.3 | | |
| Encapsulates as Example 47 | 0 | 5 | 5 | — | — | 6 | — | — |
| Encapsulates as described in example 26 | 3 | | | 10 | | | | |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine)[3] | To pH 8.0 for liquids To RA >5.0 for powders | | | | | | | |
| Solvents (1,2 propanediol, ethanol), Sulfate | To 100p | | | | | | | |

[1] Polyethylenimine (MW = 600) with 20 ethoxylate groups per —NH.
[3] RA = Reserve Alkalinity (g NaOH/dose)

Example 52

Liquid Laundry Detergent

| | Liquid Detergent Compositions | | | |
|---|---|---|---|---|
| Ingredient | 52A (Comparative) % | 52B % | 52C % | 52D % |
| Linear Alkylbenzene sulfonic acid[1] | 15 | 15 | 12 | 12 |
| C12-14 alkyl ethoxy 3 sulfate MEA salt | 10 | 10 | 8 | 9 |
| C12-14 alkyl 7-ethoxylate | 10 | 10 | 8 | 8 |
| C14-15 alkyl 8-ethoxylate | — | — | — | — |
| C12-18 Fatty acid | 10 | 10 | 10 | 10 |
| Citric acid | 2 | 2 | 3 | 3 |
| Ethoxysulfated Hexamethylene Diamine Dimethyl Quat | — | — | — | 2.2 |
| Soil Suspending Alkoxylated Polyalkylenimine Polymer[2] | 3 | 3 | 2.2 | — |
| PEG-PVAc Polymer[3] | — | — | 0.9 | 0.9 |
| Hydroxyethane diphosphonic acid | 1.6 | 1.6 | 1.6 | 1.6 |
| Fluorescent Whitening Agent | 0.2 | 0.2 | 0.2 | 0.2 |
| 1,2 Propanediol | 6.2 | 6.2 | 8.5 | 8.5 |
| Ethanol | 1.5 | 1.5 | — | — |
| Hydrogenated castor oil derivative structurant | 0.75 (introduced via NaLAS premix) | | 0.75 (introduced via MEA LAS premix) | |
| Boric acid | 0.5 | 0.5 | 0.5 | 0.5 |
| Perfume | 1.7 | 1.7 | 1.7 | 1.7 |
| Encapsulates as Example 25 | 0 | 0.9 | 1.5 | 1.8 |
| Monoethanolamine | To pH 8.0 | | | |
| Protease enzyme | 1.5 | 1.5 | 1.5 | 1.5 |
| Amylase enzyme | 0.1 | 0.1 | 0.1 | 0.1 |
| Mannanase enzyme | 0.1 | 0.1 | 0.1 | 0.1 |
| Cellulase enzyme | — | — | 0.1 | 0.1 |
| Xyloglucanase enzyme | — | — | 0.1 | 0.1 |
| Pectate lyase | — | — | 0.1 | 0.1 |
| Water and minors (antifoam, aesthetics, . . . ) | To 100 parts | | | |

[1] Weight percentage of Linear Alkylbenzene sulfonic acid includes that which added to the composition via the premix
[2] 600 g/mol molecular weight polyethylenimine core with 20 ethoxylate groups per —NH.
[3] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 53

Shampoo Formulation

| Ingredient | % by Weight |
|---|---|
| Ammonium Laureth Sulfate (AE$_3$S) | 6.00 |
| Ammonium Lauryl Sulfate (ALS) | 10.00 |
| Laureth-4 Alcohol | 0.90 |
| Trihydroxystearin[7] | 0.10 |
| Perfume | 1 |
| Encapsulates as disclosed in Example 25 | 3.8 |
| Encapsulates as disclosed in Example 42 | 2 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone[9, 10, 11] | 1.00[9] |
| Water and Minors (QS to 100%) | Balance |

Examples 54

Hard Surface Cleaner Bathroom Composition

| % Weight | 54A | 54B | 54C |
|---|---|---|---|
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Encapsulates as disclosed in Example 5 | 1 | 1.2 | 1.5 |
| Encapsulates as disclosed in Example 4 | 5 | 4 | 3 |
| Encapsulates as disclosed in Example 6 | 15 | 18 | 10 |
| Water | Balance | Balance | Balance |

Example 55

Hard Surface Cleaner Bathroom Composition (Cont.)

| % Weight | 55A | 55B | 55C |
|---|---|---|---|
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Encapsulates as disclosed in Example 26 | 5 | 4.5 | 3 |
| Water | Balance | Balance | Balance |

Example 56

Hand-dishwashing Detergent Compositions

| % Weight | 56A | 56B | 56C |
|---|---|---|---|
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Encapsulates as disclosed in Example 7 | 0.5 | 0.9 | 0.3 |
| Water (+ minor e.g.; pH adjusted to 10.5) | Balance | Balance | Balance |

Example 57

General Degreaser Composition

| % Weight | 57A | 57B |
|---|---|---|
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| Perfume | 0.5 | 1 |
| Encapsulates as disclosed in Example 5 | 10 | 15 |
| Water (+ minor e.g.; pH adjusted to alkaline pH) | Balance | Balance |

Example 58

Scouring Composition

| % Weight | 58A | 58B | 58C |
|---|---|---|---|
| Sodium C13-16 paraffin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Encapsulates as disclosed in Example 5 | 4.0 | 2.5 | 1.2 |
| Water | Balance | Balance | Balance |

Example 59

Liquid Glass Cleaner

| % Weight | 59A | 59B |
|---|---|---|
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Perfume | 0.3 | 0.3 |
| Encapsulates as disclosed in Example 2 | 10 | 5 |
| Water (+minor) | Balance | Balance |

Example 60

Fabric Refresher Compositions

|  | 60A | 60B | 60C | 60D | 60E | 60F | 60G |
|---|---|---|---|---|---|---|---|
| Polysaccharide (Xanthan Gum, Keltrol CG-SFT ® Kelco) | 0.05 | 0.07 | 0.03 | 0.05 | 0.07 | 0.05 | 0.02 |
| Lupasol WF CAS 9002-98-6 | 0.070 | 0.070 | 0.015 | 0.035 | 0 | 0.035 | 0.0525 |
| Diethylene Glycol | 0.175 | 0.175 | 0.070 | 0.175 | 0.175 | 0.175 | 0.170 |
| Perfume | 0.2102 | 0.4880 | 0.020 | 0.236 | 0.655 | 0.655 | 0.655 |
| Encapsulates as disclosed in Example 25 | 0.6 | 0.6 | 0.3 | 0.3 | 2 | | 0.3 |
| Encapsulates as disclosed in Example 26 | | 0.6 | | 0.9 | | 1.5 | |
| Hydroxypropyl Beta CD | 0.630 | 0.630 | 0.630 | 0 | 0.630 | 0.630 | 0.630 |
| Basophor ELH 60 | 0 | 0.050 | 0.050 | 0.050 | 0.050 | 0.050 | 0.050 |
| Uniquat 2250 | 0 | 0.060 | 0 | 0.060 | 0.060 | 0.060 | 0.060 |
| Bardac 2250J | 0.139 | | 0.100 | 0 | 0 | 0 | 0 |
| Silwet L-7600 | 0.100 | 0.100 | 0.175 | 0.100 | 0.100 | 0.100 | 0.100 |
| Citric Acid | 0.045 | 0.015 | 0.015 | 0.015 | 0.015 | 0.015 | 0.15 |
| Maleic Acid CAS 110-16-7 | 0 | 0.050 | 0.060 | 0.050 | 0.050 | 0.050 | 0.050 |
| ACES | 0.100 | 0 | 0 | 0 | 0 | 0 | 0 |
| Sodium Hydroxide | 0 | 0 | 0 | 0.020 | 0.020 | 0.020 | 0.020 |
| Koralone B-119 | 0 | 0.0150 | 0 | 0.015 | 0.015 | 0.015 | 0.015 |
| Ethanol | 3.000 | 3.000 | 3.000 | 3.000 | 3.000 | 3.000 | 3.000 |
| Water | Balance | Balance | Balance | Balance | Balance | Balance | Balance |

Example 61

All Purpose Cleaner

| % Weight | 61A | 61B | 61C | 61D |
|---|---|---|---|---|
| C9-C11 EO8 (Neodol 91-8 ®) | 4 | 3.5 | 5 | 6 |
| Alkyl Benzene sulfonate | | 1.5 | 1.0 | 2.5 |
| Coconut Fatty Acid | | 0.1 | 0.2 | 0.4 |
| Sodium Hydroxide | 0.16 | 0.2 | 0.3 | 0.38 |
| Koralone | 0.05 | 0.05 | 0.05 | 0.01 |
| Citric Acid | 0.6 | 0.5 | 0.5 | 0.4 |
| Polysaccharide (Xanthan Gum, Keltrol CG-SFT ® Kelco) | 0.25 | 0.25 | 0.25 | 0.25 |
| Perfume | 0.5 | 0.5 | 0.5 | 1 |
| Encapsulates as disclosed in Example 6 | 10 | 10 | 6 | 6 |
| DTPA | 0.25 | 0.25 | 0.25 | 0.25 |
| Water | Balance | balance | Balance | Balance |

Example 62

Body Cleansing Composition

The microcapsules of Example 42, 43, 44 are formulated into a body cleansing composition.

|  | 62A | 62B | 62C | 62D |
|---|---|---|---|---|
| I: Cleansing Phase Composition | | | | |
| Sodium Trideceth Sulfate (sulfated from Iconol TDA-3 (BASF Corp.) to >95% sulfate) | 5.9 | 5.9 | 5.9 | 5.9 |
| Sodium Lauryl Sulfate (Procter and Gamble) | 5.9 | 5.9 | 5.9 | 5.9 |
| Sodium Lauroamphoacetate (Cognis Chemical Corp.,) | 3.6 | 3.6 | 3.6 | 3.6 |
| Guar Hydroxypropyltrimonium Chloride (N-Hance 3196 from Aqualon) | 0.3 | 0.3 | 0.7 | 0.7 |
| Stabylen 30 (Acrylates/Vinyl Isodecanoate, 3V) | 0.33 | 0.33 | 0.33 | 0.33 |

-continued

|  | 62A | 62B | 62C | 62D |
|---|---|---|---|---|
| Sodium Chloride | 3.75 | 3.75 | 3.75 | 3.75 |
| Trideceth-3 (Iconal TDA-3 from BASF Corp.) | 1.75 | 1.75 | 1.75 | 1.75 |
| Methyl chloro isothiazolinone and methyl isothiazolinone (Kathon CG, Rohm & Haas) | 0.033 | 0.033 | 0.033 | 0.033 |
| EDTA (Dissolvine NA 2x) | 0.15 | 0.15 | 0.15 | 0.15 |
| Sodium Benzoate | 0.2 | 0.2 | 0.2 | 0.2 |
| Citric Acid, titrate | pH = 5.7 ± 0.2 | pH = 5.7 ± 0.2 | pH = 5.7 ± 0.2 | pH = 5.7 ± 0.2 |
| Scent A | 0.4 | 0.0 | 0.0 | 0.0 |
| Encapsulates as disclosed in example 42 | None | 1.45 | | |
| Encapsulates as disclosed in example 43 | | | 1.40 | |
| Encapsulates as disclosed in example 44 | | | | 1.40 |
| Water and Minors (NaOH) | Q.S. | Q.S. | Q.S. | Q.S. |
| II: Benefit Phase Composition | | | | |
| Petrolatum (G2218 from Sonnerbonn) | 60 | 60 | 60 | 60 |
| Mineral Oil (Hydrobrite 1000 from Sonnerbonn) | 20 | 20 | 20 | 20 |
| III: Surfactant Phase:Benefit Phase Blending Ratio | 50:50 | 50:50 | 50:50 | 50:50 |

Example 63

Rinse-off Conditioner

The following procedure is used to make a 500 gram batch of rinse-off conditioner. 14.24 grams of Genamin KDMP flakes are added to 410 grams of preheated water at 95 degrees Centigrade, in a 1 liter stainless steel vessel that is submerged in a water bath at 92 degrees Centigrade. The contents of the 1 liter vessel is held under agitation at 350 rpm using a IKA mixer, and a turbine agitator. A transparent solution is obtained after 5 minutes. Then, 9.3 grams of cetyl alcohol flakes, and 23.2 grams of stearyl alcohol flakes are added to the stainless steel vessel, with temperature of the contents controlled to 75-85 degrees Centigrade. Agitation is increased to 500 RPM. After 10 minutes, the following ingredients are added to the stainless steel vessel: 0.64 grams of Dissolvine EDTA acid, 6.8 grams of a 1 wt % sodium hydroxide solution, 2 g of Benzyl Alcohol, and 0.17 grams of Kathon CG preservative (methylchloroisothiazolinone and methylisothiazolinone). The contents are mixed for 2 minutes. The stainless steel reactor is then removed from the constant temperature water bath, and then the contents are cooled to 60 degrees centigrade using a cold water bath. The stainless steel reactor is placed under a IKA mill. 17.5 grams of Aminosilicone (Momentive Performance Chemicals, viscosity of 10,000 mPa·s) is premixed with 5.0 grams of the encapsulates as disclosed in the Example 42, and then slowly added to the stainless steel vessel, with the mill operating at 20,000 RPM. A spatula is used to assure that all of the material is overturned in the vessel. Milling is continued for 7 minutes at 55 degrees Centigrade. Finally, 0.25 grams of panthenyl ethyl ether and 0.50 grams of panthenol are added to the vessel, and agitated for 2 minutes. The conditioner viscosity and microstructure are characterized to assure that the conditioner formulation meets product design specifications.

Example 64

Leave-on Conditioner

A typical composition of a leave-on conditioner formulation is given in the following table:

| Components | Ex. II (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Encapsulates as disclosed in Example 25 | 1.5-6 |
| Encapsulates as disclosed in example 42 | 0.5-3 |
| Preservatives | 0.40-0.60 |

Example 65

Skin Lotion

|  | 65A | 65B | 65C |
|---|---|---|---|
| PHASE A | | | |
| DC-9040[1] | 8.6 | 3 | 5 |
| Dimethicone | 4.09 | 4 | 4 |

|  | 65A | 65B | 65C |
|---|---|---|---|
| Polymethylsilsesquioxane[2] | 4.09 | 4 | 4 |
| Cyclomethicone | 11.43 | 0.5 | 11.33 |
| KSG-210[3] | 5.37 | 5.25 | 5.4 |
| Polyethylene wax[4] | 3.54 |  | 2.05 |
| DC-2503 Cosmetic Wax[5] | 7.08 | 10 | 3.77 |
| Hydrophobic TiO2 |  | 0.5 |  |
| Iron oxide coated Mica |  |  | 0.65 |
| TiO2 Coated Mica | 1 | 1 |  |
| Encapsulates as disclosed in Example 42 | 1 | 1.5 | 1.2 |
| PHASE B |  |  |  |
| Glycerin | 10 | 10 | 10 |
| Dexpanthenol | 0.5 | 0.5 | 0.5 |
| Pentylene Glycol | 3 | 3 | 3 |
| Hexamidine Diisethionate[6] | 0.1 | 0.1 | 0.1 |
| Niacinamide[7] | 5 | 5 | 5 |
| Methylparaben | 0.2 | 0.2 | 0.2 |
| Ethylparaben | 0.05 | 0.05 | 0.05 |
| Sodium Citrate | 0.2 | 0.2 | 0.2 |
| Citric Acid | 0.03 | 0.03 | 0.03 |
| Sodium Benzoate | 0.05 | 0.05 | 0.05 |
| Sodium Chloride | 0.5 | 0.5 | 0.5 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1]12.5% Dimethicone Crosspolymer in Cyclopentasiloxane. Available from Dow Corning™.
[2]E.g., Tospearl™ 145A or Tospearl 2000. Available from GE Toshiba Silicone™.
[3]25% Dimethicone PEG-10/15 Crosspolymer in Dimethicone. Available from Shin-Etsu™.
[4]Jeenate™ 3H polyethylene wax from Jeen™
[5]Stearyl Dimethicone. Available from Dow Corning.
[6]Hexamidine diisethionate, available from Laboratoires Serobiologiques.
[7]Additionally or alternatively, the composition may comprise one or more other skin care actives, their salts and derivatives, as disclosed herein, in amounts also disclosed herein as would be deemed suitable by one of skill in the art.

For the examples above, in a suitable container, combine the ingredients of Phase A. In a separate suitable container, combine the ingredients of Phase B. Heat each phase to 75° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 75° C. and store at room temperature. Alternatively, continuing to stir the mixture as temperature decreases results in lower observed hardness values at 21 and 33° C.

Example 66

Microcapsules in Antiperspirant/Deodorant

| Ingredient | Comparative Example 66A | Comparative Example 66B[9] | Example 66C | Example 66D | Example 66E |
|---|---|---|---|---|---|
| Part I: Partial Continuous Phase |  |  |  |  |  |
| Hexamethyldisiloxane[1] | 22.65 | 21.25 | 21.25 | 21.25 | 21.25 |
| DC5200[2] | 1.20 | 1.20 | 1.20 | 1.20 |  |
| Fragrance | 0.35 | 1.25 | 1.25 | 1.25 | 1.25 |
| Encapsulates as disclosed Example 42 | 1.00 | 1.00 | 1.00 | 1.00 | 1.00 |
| Shin Etsu KF 6038[3] |  |  |  |  | 1.20 |
| Part II: Disperse Phase |  |  |  |  |  |
| ACH (40% solution)[4] | 40.00 | 55.0 |  |  |  |
| IACH (34% solution)[5] |  | 2.30 | 49.00 |  |  |
| ZAG (30% solution)[6] |  |  |  | 52.30 | 52.30 |
| propylene glycol | 5.00 |  | 5.00 | 5.00 | 5.00 |
| water | 12.30 |  | 3.30 |  |  |
| Part III: Structurant Plus Remainder of Continuous Phase |  |  |  |  |  |
| FinSolve TN | 6.50 | 6.00 | 6.50 | 6.00 | 6.50 |
| Ozocrite Wax |  |  |  |  | 12.00 |
| Performalene PL[7] | 11.00 | 11.00 | 12.00 | 12.00 |  |
| Aqueous Phase Conductivity (mS/cm) | 37.7 | 79.5 | 40.5 | 60.3 | 60.3 |

[1]DC 246 fluid from Dow Corning
[2]from Dow Corning
[3]from Shinetsu
[4]Standard aluminum chlorohydrate solution
[5]IACH solution stabilized with calcium
[6]IZAG solution stabilized with calcium
[7]from New Phase Technologies
[9]emulsion broke when manufacturing this composition The above examples 66A through 66E can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

| Ingredient | 66F | 66G | 66H | 66I | 66J |
|---|---|---|---|---|---|
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| glycerine | | | | 10 | |
| PEG-8 | | | | 20 | |
| ethanol | | | | | QS |
| water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragramce | 0.5 | 0.5 | 0.5 | 0.5 | 0.5 |
| Fragrance capsules of Example 26 | 3 | 2.5 | 1.5 | 1.5 | 1.8 |
| dihydromyrcenol | 0.3 | .1 | 0.3 | 0.5 | .1 |
| linalool | 0.2 | .15 | 0.2 | 0.25 | .15 |
| Propellant (1,1 difluoroethane) | | | | | 40 |

QS - indicates that this material is used to bring the total to 100%.

Examples 66F to 66I can be made as follows: all ingredients except the fragrance, linalool, and dihydromyrcenol are combined in a suitable container and heated to about 85° C. to form a homogenous liquid. The solution is then cooled to about 62° C. and then the fragrance, linalool, and dihydromyrcenol are added. The mixture is then poured into an appropriate container and allowed to solidify up cooling to ambient temperature.

Example 66J can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally, an appropriate actuator is connected to the valve to allow dispensing of the product.

Example 67

Examples of Granular Laundry Detergent Compositions Comprising the Perfume Composition are Included Below

| | % w/w of laundry detergent compositions | | | | | | | |
|---|---|---|---|---|---|---|---|---|
| Raw material | 67A | 67B | 67C | 67D | 67E | 67F | 67G | 67H |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Encapsulates as disclosed in Example 47 | 1.5 | 6 | 3 | 2.5 | 4.3 | 15 | 12 | 4 |
| Water & Miscellaneous | Balance to 100% | | | | | | | |

The equipment and materials described in Examples 1 through to 67 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An encapsulate comprising a shell and a core, said core comprising a core material selected from the group consisting of a perfume, a silicone, a biocontrol agent, an antimicrobial, a flavor, a heating or cooling agent, a drug, a sun screen and mixtures thereof; said shell encapsulating said core and said shell comprising a cross-linked polymer having a main chain and an electromagnetic radiation sensitive moiety; wherein said electromagnetic radiation sensitive moiety is incorporated into the main chain of the polymer, and is sensitive to a species of electromagnetic radiation selected from the group consisting of infrared radiation, visible light, ultraviolet radiation and mixtures thereof; and wherein said electromagnetic radiation sensitive moiety is provided by a monomer selected from the group consisting of 4-[(E)-(4-chlorocarbonylphenyl)azo] benzoyl chloride, 4-[(E)-(4-aminophenyl)azo]aniline, [4-[(E)-[4-(aminomethyl)phenyl]azo]phenyl]methanamine, (E)-bis(4-vinylphenyl)diazene, [4-[(E)-[4-(hydroxymethyl)phenyl]azo]phenyl]methanol, 4-[(E)-(4-hydroxyphenyl)azo]phenol, 4-[(E)-[4-chlorocarbonyl-2-(diethylamino)phenyl]azo]-3-(diethylamino)benzoyl chloride, 4-[(E)-(4-chlorocarbonyl-2-pyrrolidin-1-yl-phenyl)azo]-3-pyrrolidin-1-yl-benzoyl chloride, 4-[(E)-(4-formylphenyl)azo] benzaldehyde, 4-[(E)-(4-chlorocarbonyl-2,6-dimethoxyphenyl)azo]-3,5-dimethoxy-benzoyl chloride, 4-methacryloxy-azobenzene, 4,4'-di(methacrylamido)-azobenzene, 4,4'-dimethacryloxy-azobenzene, 4-hydroxymethyl-azobenzene, 4-methacrylxoxymethyl-azobenzene, 4,4'-dimethacryloxymethyl-azobenzene, 4,4'-bis(chlorocarbonyl)azobenzene, and mixtures thereof.

2. The encapsulate of claim 1, wherein said cross-linked polymer is selected from the group consisting of polyamides, aminoplast polymers polyurethanes, polyureas, polycarbonates, polyacrylates, polyesters, and mixtures thereof.

3. A composition comprising one or more encapsulates according to claim 1 and an adjunct ingredient.

4. The composition of claim 3, comprising, based on total composition weight from about 0.1% to about 25% of said encapsulate.

5. The encapsulate of claim 1, wherein said shell of said encapsulate, upon exposure of said encapsulate to ultraviolet light for about four hours, permits release of said core material from said core, thereby increasing the amount of core material in a surrounding environment.

6. The encapsulate of claim 1, wherein said electromagnetic radiation sensitive moiety is provided by a monomer selected from the group consisting of 4-[(E)-(4-chlorocarbonylphenyl)azo]benzoyl chloride, 4-[(E)-(4-aminophenyl)azo]aniline, (E)-bis(4-vinylphenyl)diazene, and mixtures thereof.

7. The encapsulate of claim 1, wherein said cross-linked polymer is a polyamide.

8. The encapsulate of claim 1, wherein said cross-linked polymer is a polyacrylate.

9. The encapsulate of claim 1, wherein said cross-linked polymer is an aminoplast polymer.

* * * * *